United States Patent
Rasmussen et al.

(10) Patent No.: US 10,292,847 B2
(45) Date of Patent: May 21, 2019

(54) SYSTEM AND METHOD FOR THE SEQUENTIAL EXPANSION OF A MEDICAL DEVICE

(71) Applicant: COOK MEDICAL TECHNOLOGIES LLC, Bloomington, IN (US)

(72) Inventors: Erik E. Rasmussen, Slagelse (DK); Bent Oehlenschlaeger, Lille Skensved (DK); Annette Petersen, Naestved (DK)

(73) Assignee: Cook Medical Technologies LLC, Bloomington, IN (US)

( * ) Notice: Subject to any disclaimer, the term of this patent is extended or adjusted under 35 U.S.C. 154(b) by 371 days.

(21) Appl. No.: 15/071,650

(22) Filed: Mar. 16, 2016

(65) Prior Publication Data
US 2016/0270935 A1 Sep. 22, 2016

(30) Foreign Application Priority Data
Mar. 16, 2015 (GB) .................................... 1504414.2

(51) Int. Cl.
*A61F 2/06* (2013.01)
*A61F 2/95* (2013.01)
(Continued)

(52) U.S. Cl.
CPC .................. *A61F 2/95* (2013.01); *A61F 2/07* (2013.01); *A61F 2/844* (2013.01); *A61F 2/89* (2013.01);
(Continued)

(58) Field of Classification Search
CPC .... A61F 2/07; A61F 2/95; A61F 2/962; A61F 2/966; A61F 2002/9505; A61F 2002/9511; A61F 2002/9665
(Continued)

(56) References Cited

U.S. PATENT DOCUMENTS

2002/0151956 A1  10/2002  Chobotov et al.
2002/0177890 A1  11/2002  Lenker
(Continued)

FOREIGN PATENT DOCUMENTS

DE  102012101103 B3  7/2013
EP  2735283 A1  5/2014
(Continued)

OTHER PUBLICATIONS

Examination Report for corresponding Great Britain Appln. No. GB1504414.2, dated Aug. 22, 2016, 2 pages.
(Continued)

*Primary Examiner* — Melanie R Tyson
(74) *Attorney, Agent, or Firm* — Brinks Gilson & Lione

(57) ABSTRACT

A system for deploying a stent graft includes a stent graft. The stent graft has a tubular structure and includes first and second end stents and at least one stent between the first and second end stents. The system also includes a plurality of constraining mechanisms arranged along the length of the stent graft constraining the stents of the stent graft, and an actuation mechanism configured to release the plurality of constraining mechanisms in order from the first end to the second end of the stent graft and circumferentially sequentially from about the stents.

20 Claims, 29 Drawing Sheets

(51) Int. Cl.
  *A61F 2/966* (2013.01)
  *A61F 2/07* (2013.01)
  *A61F 2/844* (2013.01)
  *A61F 2/89* (2013.01)

(52) U.S. Cl.
  CPC ........ *A61F 2/966* (2013.01); *A61F 2002/075* (2013.01); *A61F 2002/9511* (2013.01); *A61F 2002/9665* (2013.01)

(58) Field of Classification Search
  USPC ...................................... 623/1.11, 1.12, 1.13
  See application file for complete search history.

(56) References Cited

U.S. PATENT DOCUMENTS

| | | | |
|---|---|---|---|
| 2011/0118816 A1* | 5/2011 | Jensen | A61F 2/07 623/1.11 |
| 2013/0268048 A1 | 10/2013 | Watson et al. | |
| 2013/0289713 A1 | 10/2013 | Pearson et al. | |
| 2014/0336745 A1 | 11/2014 | Barthold et al. | |

FOREIGN PATENT DOCUMENTS

| | | |
|---|---|---|
| EP | 2749251 A1 | 7/2014 |
| JP | 2012-524608 A | 10/2012 |
| WO | WO 2011/062858 A1 | 5/2011 |
| WO | WO 2016/115007 A1 | 7/2016 |

OTHER PUBLICATIONS

Examination Report for corresponding Great Britain Appln. No. GB1504414.2, dated Apr. 19, 2017, 3 pages.
Examination Report under Section 18(3) in corresponding Great Britain Application No. GB1504414.2, dated Sep. 6, 2017, 2 pages.
Examination Report under Section 18(3) in corresponding Great Britain Application No. GB1504414.2, dated Feb. 12, 2018, 3 pages.
Extended European Search Report for corresponding EP 16275044 dated May 31, 2016, 6 pages.
Search and Examination Report for corresponding Great Britain Appln. No. GB1504414.2, dated Aug. 27, 2015, 6 pages.
Examination Report for corresponding Great Britain Appln. No. GB1504414.2, dated Apr. 13, 2016, 3 pages.
Intention to Grant Communication from corresponding EP Application No. 16275044.2, dated Dec. 1, 2016, 6 pages.

* cited by examiner

SYSTEM AND METHOD FOR THE SEQUENTIAL EXPANSION OF A MEDICAL DEVICE

RELATED APPLICATIONS

The present patent document claims the benefit of priority to Great Britain Patent Application No. 1504414.2, filed Mar. 16, 2015, and entitled "MEDICAL DEVICE ASSEMBLY WITH CONSTRICTION MECHANISM," the entire contents of each of which are incorporated herein by reference.

TECHNICAL FIELD

The present invention relates to assemblies including implantable medical devices, for example stent grafts.

BACKGROUND

Stent grafts are often positioned in the descending aorta, for example for treating aneurysms. However, sometimes it is necessary to implant a stent graft in the ascending aorta that is in close proximity to the aortic valve. Positioning a stent graft in the ascending aorta requires maneuvering around the aortic arch and into the ascending aorta. Passing of the deployment device over the aortic arch can cause loss of the control over the deployment device because of the significant curvature of the aortic arch. Furthermore, as the ascending aorta is in close proximity to the aortic valve, it is important when positioning stent grafts in the ascending aorta that they are placed accurately without gaps between the aorta and the graft.

SUMMARY

The present invention provides an implantable medical device assembly and method for deployment thereof that permits accurate and precise placement of an implantable medical device, such as a self-expanding stent graft, in or adjacent a curved body vessel.

The assembly for deploying a stent graft includes a stent graft having a first end, a second end, a first end stent at the first end of the stent graft, a second end stent at the second end of the stent graft, and at least one intermediate stent between the first end stent and the second end stent. A plurality of constraining mechanisms are arranged along the length of the stent graft and configured to constrain all of the stents of the stent graft that are releasable, and an actuation mechanism is operable to release the constraining mechanisms. The stents are released from constraining the diameter of the stent graft in order from the first (proximal) end to the second (distal) end. Further, at least a proximal covered stent and the intermediate stents are released in a circumferentially sequential fashion.

The constraining mechanisms may be a suture thread or other circumferential filament that is circumferentially engaged about the circumference of the proximal covered stent, a distal covered stent and each of the intermediate stents. The proximal and distal stents may have a single constraining mechanism about their proximal and distal apices, respectively. The intermediate stents may have a plurality of constraining mechanisms, such as a first constraining mechanism at or near the proximal apices of each of the stents and a second constraining mechanism at or near the distal apices of the stent.

Trigger wires or similar release mechanisms extend from the operator end of the delivery device and engage the constraining mechanisms. The release wires may of different lengths or staggered. In operation, the release wires are disengaged from the constraining mechanisms such that the each stent is released sequentially from the proximal end of the stent graft to the distal end of the stent graft in order and in a circumferentially sequential fashion.

DETAILED DESCRIPTION

Figure 1:
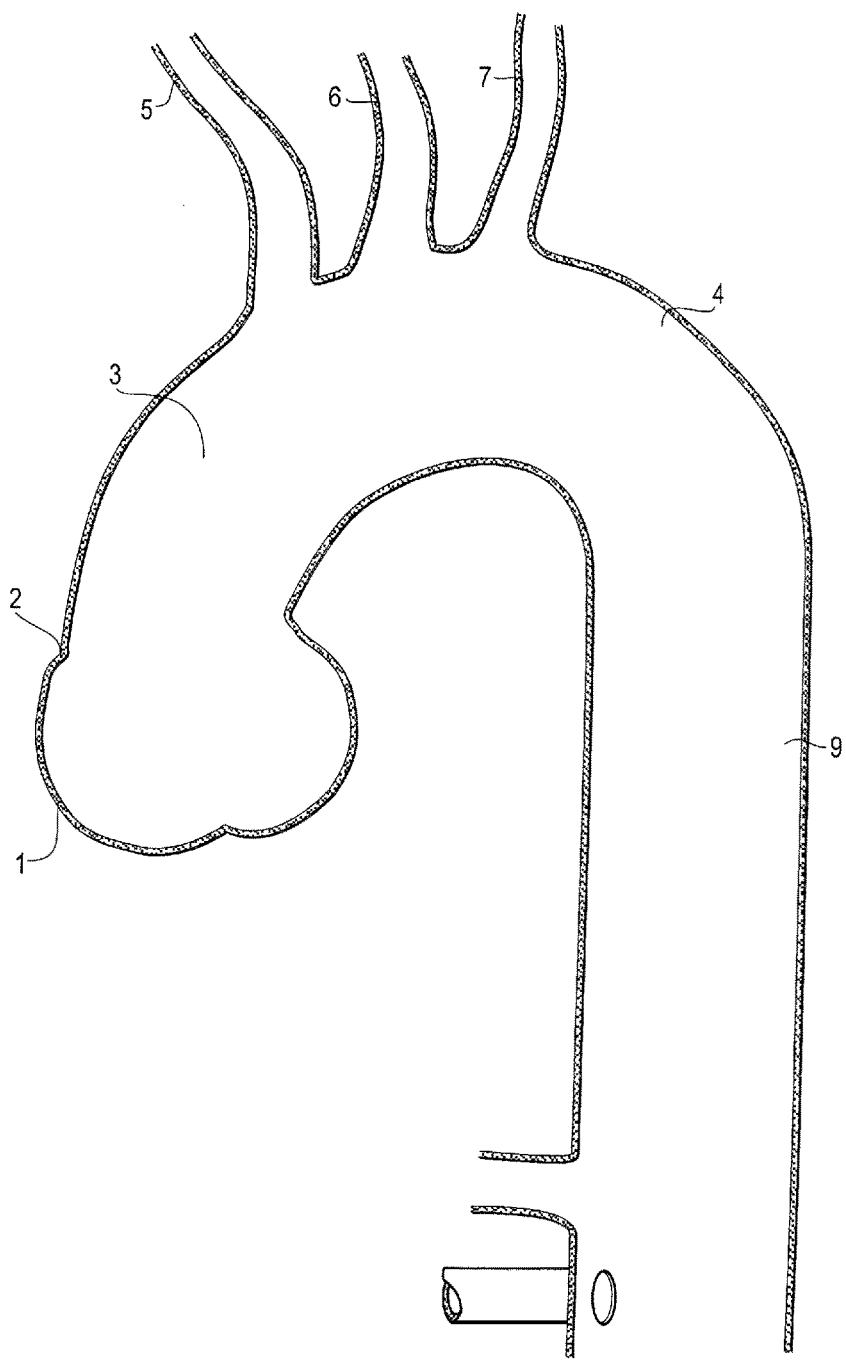
FIG. 1 shows a schematic view of an aorta, including the abdominal aorta, the aortic arch and the thoracic aorta.

Described below are various embodiments of the assembly of the invention. It is to be understood that the drawings are not to scale and are intended to be merely illustrative of the features and elements of the assembly and its components taught herein.

In this description, when referring to a deployment assembly, the term distal is used to refer to an end of the delivery device or a component of the delivery which in use is furthest from the surgeon during the medical procedure, including within a patient. The term proximal is used to refer to an end of a component closest to the surgeon and in practice in or adjacent an external manipulation part of the deployment or treatment assembly.

On the other hand, when referring to an implantable medical device itself, such as a stent or stent graft, the term proximal refers to a location which in use is closest to the patient's heart, in the case of a vascular implant, and the term distal refers to a location furthest from the patient's heart.

The inventors have discovered that by providing a stent graft in which all of the stents can be released sequentially in order from the first to the second end and in a circumferentially staggered fashion, the stent graft can be deployed in a very smooth manner, in many cases avoiding significant jolts or jumps which might cause the stent graft to move out of position. This is particularly advantageous in the ascending aorta where accuracy of position is important owing to the closeness of the aortic valve, the closeness of the arch arteries, and the curvature of the ascending aorta.

In addition, because all the stents are constrained, a deployment sheath can be completely removed from the medical device without portions of the medical device springing open too far. Hence, the stent graft can easily be repositioned after withdrawal of the sheath, to ensure that it is in the correct position before full deployment.

An actuation mechanism to release the stent graft from its diametrically constrained condition and from the delivery device can include a retractable sheath and at least one release wire or rod, preferably a plurality of release wires or rods. The release wires or rods may each be the same length or different lengths. First ends of the release wires or rods may be held at a distal (operator) end of the delivery device at different longitudinal distances from the stent graft, whereby the stent graft is positioned between the first ends of release wires and a release wire actuator. This enables the release wires to be withdrawn together but to release each of the constraining mechanisms in stages. In some embodiments, a longitudinal distance between the held ends of a first release wire or rod of the actuation mechanism and a last release wire or rod of the actuation mechanism may be less than a minimum longitudinal distance between couplings of adjacent constraining mechanisms.

The stent graft includes a generally tubular graft having a first end and a second end; wherein the stent graft has a first covered stent at the first end of the graft and a last covered stent at the second end of the graft and at least one, preferably several, intermediate stents between the first covered stent and the last covered stent. The stents are preferably self-expanding. A covered stent is a stent that is within the area of the graft; the graft may be on the inner side or the outer side of a covered stent.

Each intermediate stent, the stents between a proximal covered stent and a distal covered stent is provided with one or more constraining mechanisms including a constriction element coupled to the actuation mechanism. The first covered stent is provided with a constraining mechanism including a constriction element coupled to the actuation mechanism. It has been found that by having a said constriction element at the proximal covered stent, the proximal covered stent expands in a reliable and predictable way when the constriction element is released, so that the proximal covered stent is positioned substantially parallel to a wall of the vessel in which it is being deployed. The last covered stent may also have a constraining mechanism including a constriction element coupled to the actuation mechanism. In some embodiments, all intermediate stents of the stent graft, or all stents between the first and second end stents, are constrained by the constraining mechanisms. In some embodiments, all stents of the stent graft are constrained by the constraining mechanisms, but in other embodiments, the first and second end stents may be retained by a separate retention mechanism.

Each said constriction element may include a thread element which may be attached to the stent which the constriction element is configured to constrict. Each thread element may extend angularly or circumferentially partly around or preferably entirely around the respective stent. For example, each said thread element may extend around substantially the entire circumference of the respective stent. This may be considered to be a hoop thread. The thread elements can be single or multiple threads or filaments. In this context, angular or angularly means in an angular direction, with respect to a longitudinal axis, in a plane substantially perpendicular to the longitudinal axis. Each said thread element may restrain at least one, preferably multiple, restraining locations angularly around the stent graft by the actuation mechanism. Each said thread element can be coupled to the actuation mechanism at the respective restraining location or locations. The restraining locations associated with each said thread element may be at regular angular intervals around the stent graft.

In some embodiments, each said thread element is restrained by each release wire or rod of the actuation mechanism with each release wire or rod contributing to the constriction function of the said thread element.

In some embodiments at least one intermediate stent, preferably all intermediate stents, is provided with a constraining mechanism including one or more constriction elements, for example, a first constriction element diametrically constricting a first, for example proximal, section of the respective stent and a second constriction element constricting a second, for example distal, section of the respective stent. This can preferably constrict substantially the entire longitudinal extent of the respective intermediate stent. The first covered stent may be provided with a single said constriction element.

The same release wires of the actuation mechanism may be used to release all of the constraining mechanisms, which in embodiments includes all constraining mechanisms which couple the stent graft to a radially inner member. In other embodiments, the first and second end stents can each be provided with a constraining mechanism, which is coupled to or includes a coupling to a first set of release wires of the actuation mechanism; and the other constraining mechanisms can be coupled to or can include a coupling to a second set of release wires of the actuation mechanism. The first and second sets of release wires can be mutually exclusive whereby the first and second end stents can have constraining mechanisms that can be released independently of the other constraining mechanisms.

According to an aspect of the invention, there is provided a method of deploying a stent graft with an assembly, the assembly including:

a stent graft having a first end, a second end, a tubular structure, and a length, and including a first end stent at the first end of the stent graft, a second end stent at the second end of the stent graft, and at least one stent between the first end stent and the second end stent;

a plurality of constraining mechanisms arranged along the length of the stent graft and configured to constrain all of the stents of the stent graft, each of the constraining mechanisms being releasable; and an actuation mechanism operable to release the constraining mechanisms in order from the first end to the second end of the stent graft; the method including:

operating the assembly to advance the stent graft to a deployment site; and releasing each of the constraining mechanisms in order from the first end of the stent graft towards the second end of the stent graft.

Operating the actuation mechanism, such as by withdrawing the actuation mechanism releases each of the constraining mechanisms includes withdrawing one or more release wires or rods in a direction from the first end of the stent graft towards the second end of the stent graft.

FIG. 1 shows a schematic view of the aorta of a human body. From left to right are shown the aortic valve 1, through which blood from the heart passes, the sinotubular junction, the ascending thoracic aorta 3, the aortic arch 4, and the descending thoracic aorta 9. The aortic arch 4 includes the innominate artery 5, the left common carotid artery 6, the left subclavian artery 7.

Figure 2:
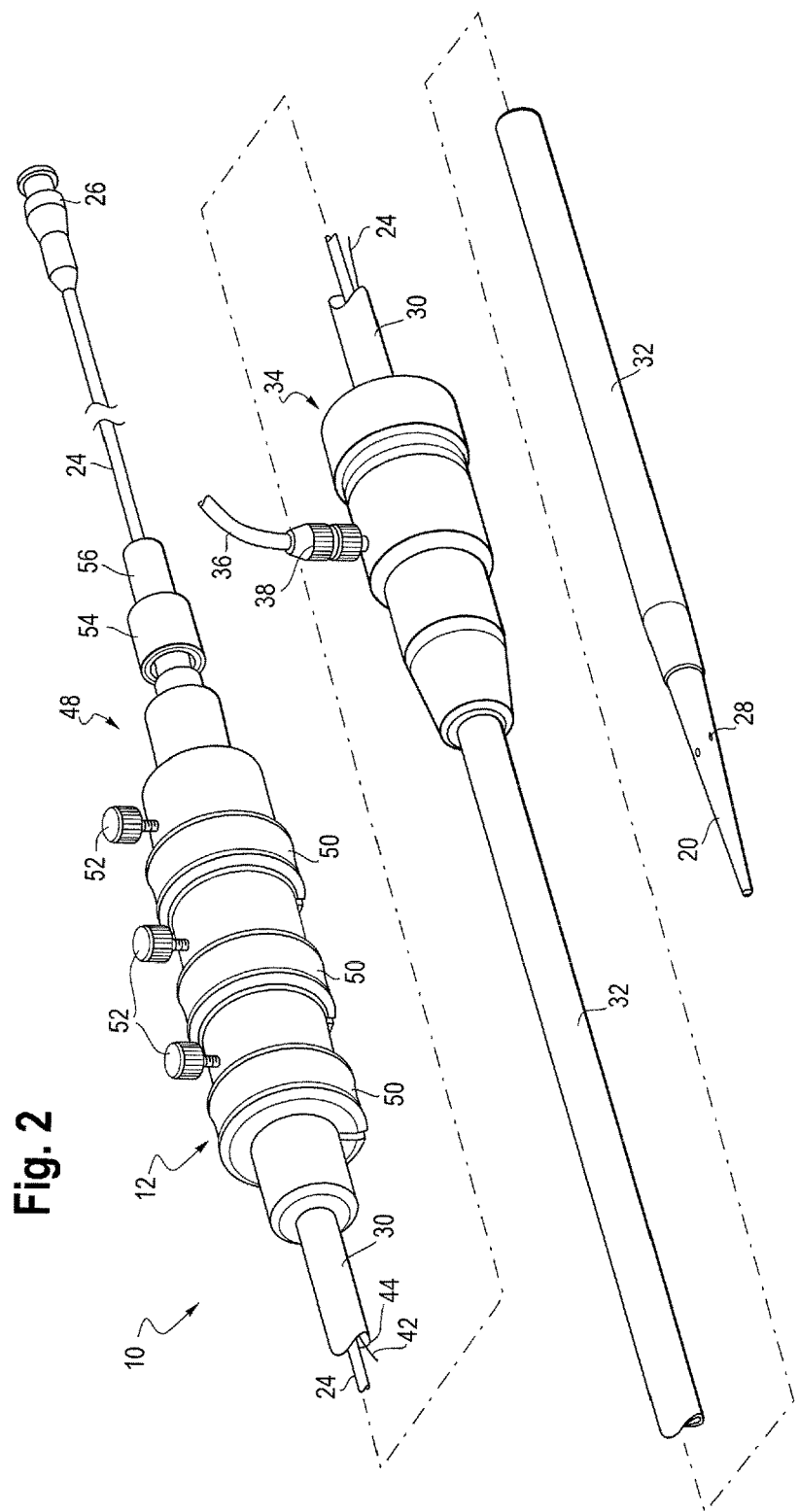
FIG. 2 shows an exemplary delivery system for an implantable medical device such as a stent graft.
Figure 3:
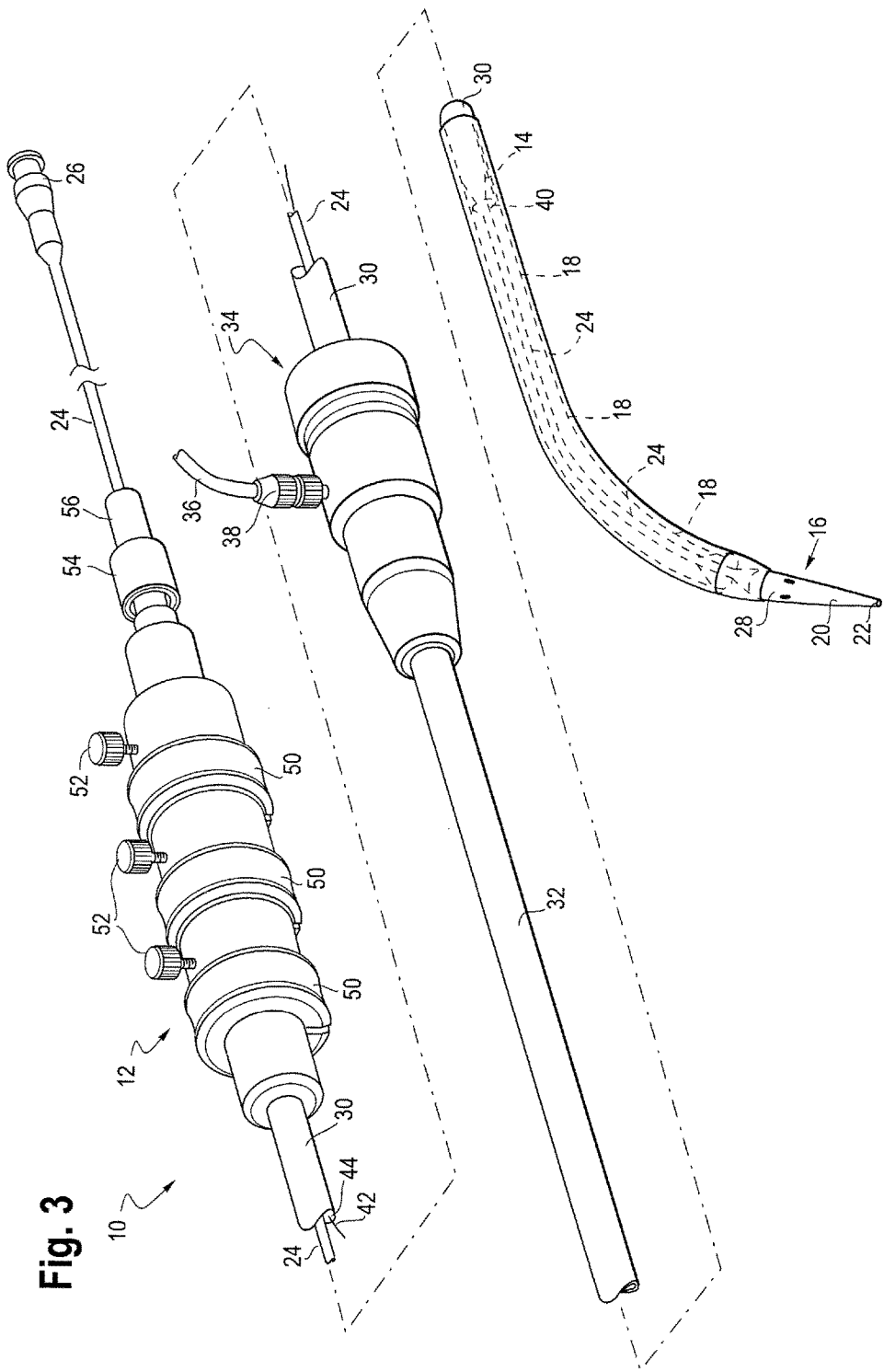
FIG. 3 shows another exemplary delivery system for an implantable medical device such as a stent graft.

FIGS. 2 and 3 show exemplary delivery systems (introducers) for an implantable medical device such as a stent graft of the present disclosure. An implant deployment assembly 10 includes an external manipulation section 12, a proximal attachment region 14 and a distal attachment region 16 (shown in FIG. 3). The proximal attachment region 14 and the distal attachment region 16 secure the two ends of an implant 18—the proximal and distal ends of the implant, respectively.

During the medical procedure to deploy the implant 18, the proximal and distal attachment regions 14 and 16 will travel through the patient's vasculature, in this example, to a desired deployment site. The external manipulation section 12 at the proximal end of the implant deployment assembly 10, which is operated by a surgeon to manipulate the introducer, remains outside of the patient throughout the procedure.

The distal attachment region 16 of the implant deployment assembly 10 includes a dilator tip 20, which is typically provided with a bore 22 therein for receiving a guide wire (not shown) of conventional type. The longitudinal bore 22 also provides a channel for the introduction of medical reagents. For example, it may be desirable to supply a contrast agent to allow angiography to be performed during placement and deployment phases of the medical procedure. In FIG. 2, the dilator tip 20 is generally straight. In FIG. 3, the dilator tip 20 is curved.

A guide wire carrier or cannula 24, conventionally made from a flexible thin walled metal tube, such as from nitinol or stainless steel, is fastened to the dilator tip 20. The guide wire carrier 24 is flexible so that the implant deployment assembly 10 can be advanced along a relatively tortuous vessel, such as a femoral artery, and so that the distal end of the implant deployment assembly 10 can be longitudinally and rotationally manipulated. The guide wire carrier 24 carries a stent 18 or other device to be implanted in the patient. The guide wire carrier 24 extends through the implant deployment assembly 10 to the manipulation section 12, terminating at a connection device 26.

The connection device 26 is designed to accept a syringe to facilitate the introduction of reagents into the guide wire carrier 24 and for this purpose is typically provided with a threaded luer lock connection.

Where provided, a pusher sheath or catheter 30 (hereinafter referred to as a pusher member), typically made from a plastics material, is mounted coaxial with and radially outside of the guide wire carrier 24. The pusher member 30 is "thick walled," that is the thickness of its wall is preferably several times greater than that of the guide wire carrier 24. In some instances, the pusher member 30 and the guide wire carrier 24 are the same component, possibly having different outer diameters at the location at which the stent 18 is to be carried.

A retractable sheath 32 extends coaxially over and radially outside of the pusher member 30. The pusher member 30 and the sheath 32 extend distally to the manipulation region 12. The implant 18 is retained in a compressed condition by the sheath 32. The sheath 32 extends proximally to a sheath manipulator and haemostatic sealing unit 34 of the external manipulation section 12. The haemostatic sealing unit 34 includes a haemostatic seal (not shown) and a side tube 36 held to the unit 34 by a conventional luer lock 38.

The sheath manipulator and haemostatic sealing unit 34 also includes a clamping collar (not shown) that clamps the sheath 32 to the haemostatic seal and a silicone seal ring (not shown) that forms a haemostatic seal around the pusher member 30. The side tube 38 facilitates the introduction of medical fluids between the pusher member 30 and the sheath 32. Saline solution is typically used.

During assembly of the implant deployment device 10, the sheath 32 is advanced over the proximal end of the dilator tip 20 of the distal attachment region 16 while the implant 18 is held in a compressed state by an external force. A suitable distal attachment (retention) section (not visible in this view) is coupled to the pusher member 30 and retains a distal end 40 of the prosthesis 18 during the procedure. The distal end of the prosthesis 18 may be provided with a loop of material (not shown) through which release wires 42 extend. The release wires also extend through an aperture (not shown in FIGS. 2 and 3) in the proximal attachment section 14 into an annular region 44 between the guide wire carrier 24 and the pusher member 30. The release wires 42 extend through the annular space 44 to the manipulation region 12 and exit the annular space 44 at one or more release wire mechanisms or actuation sections 50.

The external manipulation section 12 includes at least one release wire actuation section 50 mounted on a body 48, in turn mounted onto the pusher member 30. The guide wire carrier 24 passes through the body 48. The release wire mechanisms 50 are mounted for slidable movement on the body 48.

Clamping screws 52 prevent inadvertent early release of the prosthesis 18. A haemostatic seal (not shown) is included so that the release wires can extend out through the body 48 without unnecessary blood loss during the medical procedure.

A proximal portion of the external manipulation section 12 includes a pin vice 54 mounted onto the proximal end of the body 48. The pin vice 54 has a screw cap 56. When screwed in, vice jaws (not shown) of the pin vice 54 clamp against or engage the guide wire carrier 24. When the vice jaws are engaged, the guide wire carrier 24 can only move with the body 48 and hence it can only move with the pusher member 30. With the screw cap 56 tightened, the entire assembly can be moved together as one piece.

Once the implant deployment assembly 10 is in the desired deployment position, the sheath 32 is withdrawn and the release wire mechanisms 50 are released to allow the prosthesis 18 to expand. For some procedures, the sheath 32 may be left in place after expansion of the implant 18. The pusher member 30 and guide wire carrier 24 may be withdrawn and replaced by a further component, using the sheath 32 as a guide.

The guide wire carrier 24 can sometimes be described, both above and in the description which follows, as a center guide wire carrier, as a cannula or as a catheter and in all of the embodiments described herein it could take any of these forms. It is also to be understood that although some embodiments described below make use of a guide wire carrier as well as an introducer carrier, this is not an essential combination as it is envisaged that in some embodiments a guide wire may be carried within the introducer carrier that is without any separate guide wire carrier or cannula.

Figure 17:
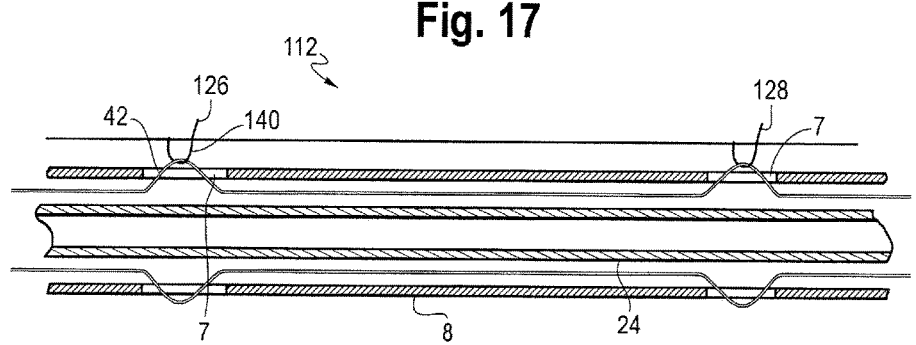
FIG. 17 is a schematic view of a portion of the stent attachment mechanisms of the invention.

As shown in FIG. 17, in the region of the medical device 18 (not shown in FIG. 17), the deployment assembly 10' has a guide wire carrier 24 and a release wire carrier 8 (typically the carrier of the introducer for carrying the medical device) located coaxially around the guide wire carrier 24, such that the guide wire carrier resides in a lumen 9 of the release wire carrier 8. In some embodiments a guide wire may be located directly in the release wire carrier 8 thus avoiding the need for a separate guide wire carrier 24. The release wires 42 pass along the annular space between the guide wire carrier 24 and the release wire carrier 8, preferably to avoid tangling with a guidewire in the guidewire carrier.

Figure 4:
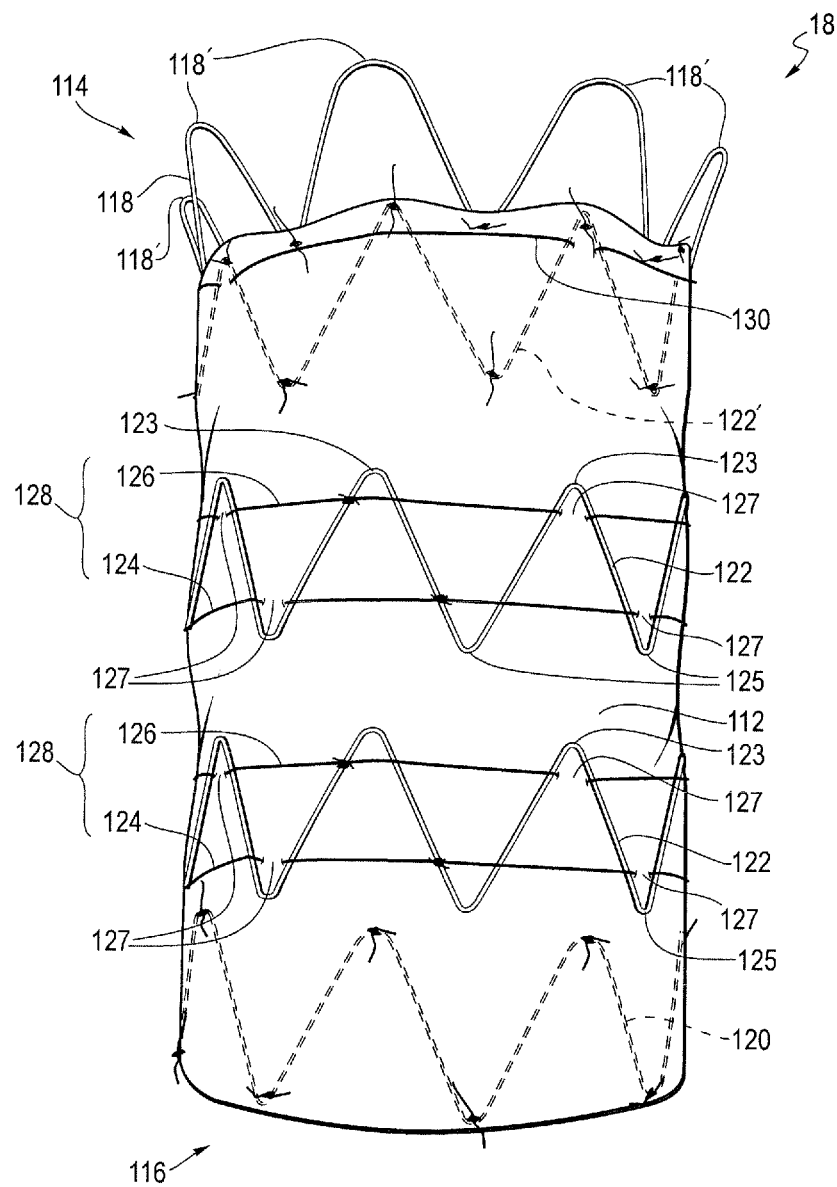
FIG. 4 shows an exemplary stent graft in accordance with the invention.
Figure 5:
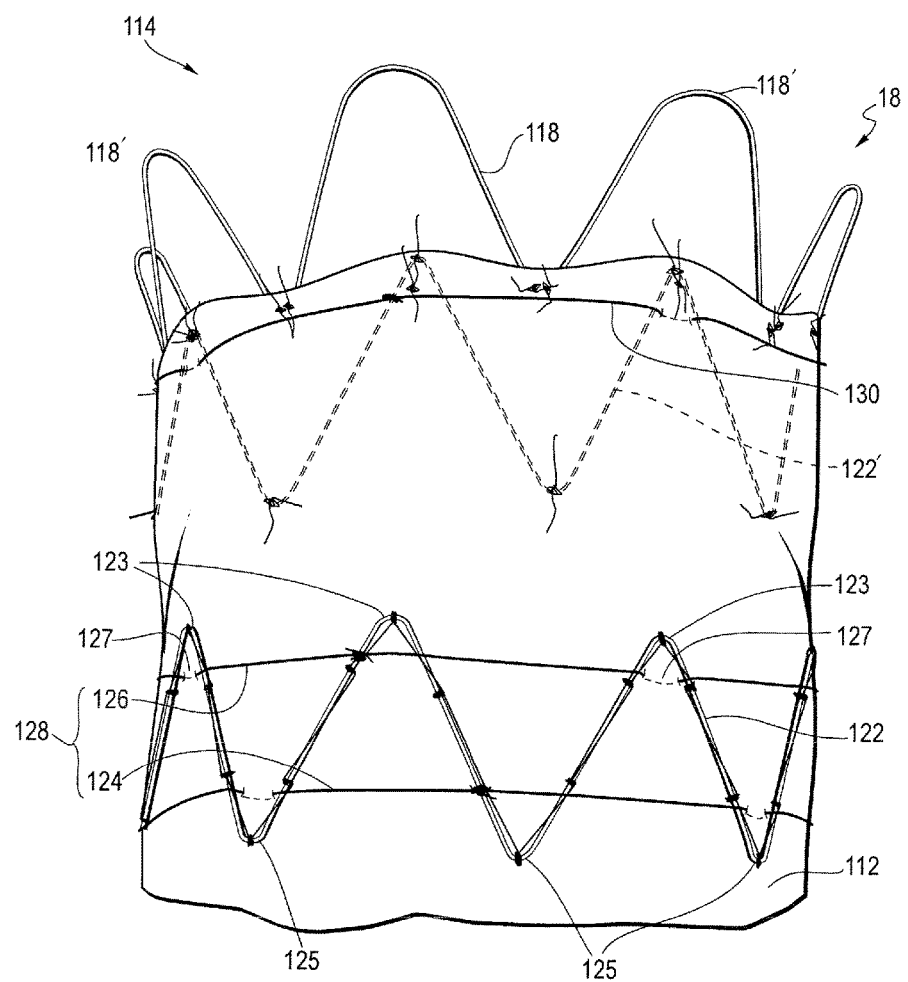
FIG. 5 is a partial view of the proximal end of the stent graft shown in FIG. 4.

FIG. 4 shows an exemplary stent graft in accordance with the invention and FIG. 5 is a partial view of the proximal end of the stent graft shown in FIG. 4. FIG. 4 shows the stent graft 18 in an expanded state as it would be after being fully deployed within a body vessel such as an ascending aorta. In the embodiment of FIG. 4, the stent graft 18 is intended for being deployed in the ascending aorta, in close proximity to the aortic valve. However, it is to be appreciated that medical devices according to other embodiments of the invention could be used for deployment in other parts of the human or animal vasculature.

The stent graft 18 of the embodiment of FIG. 4 includes a tubular graft 112 of biocompatible material with a lumen therethrough and having a longitudinal axis. The stent graft 18 has a proximal end 114 and a distal end 116. When the stent graft is placed in the ascending aorta of a patient, the proximal end 114 is configured to be closest to the heart valve. The stent graft 18 includes a proximal end stent 118 and a distal end stent 120. As shown in FIG. 4, the proximal end stent 118 is a bare stent located at and extending beyond the proximal end 114 of the stent graft 18. In one embodiment, the longitudinal length of the bare stent from proximal to distal apices is about 15 mm. In the depicted embodiment, the diameter of the bare stent tapers from a first diameter at its proximal end to a second smaller diameter at its distal end thereby forming a frusto-conical shape. The proximal end stent has proximal apices 118A and distal apices 118B. As shown, the proximal apices may have a larger radius of curvature than the distal apices so as to present an atraumatic end of the stent graft. This stent may be of the type shown and described in U.S. Pat. Nos. 9,180,030, 8,740,966 and 8,574,284, which disclosures are incorporated by reference herein in their entireties. The distal end stent 120, the proximal covered stent 122' and the intermediate stents 122 may be conventional z-stents as shown or other configurations.

The distal end stent 120 is located at the distal end 116 of the stent graft 18 but, as shown, does not extend distally beyond the distal most edge of the graft material. In other words, the distal end stent is also the last covered stent. In other embodiments, the distal end stent can be a bare stent extending beyond the distal end of the graft material of the same or similar construction as the proximal bare stent, and/or the proximal end stent can be a non-bare stent and can be the first covered stent.

As shown in FIG. 4, the stent graft 18 includes a first covered stent 122' which is a different stent from the proximal end stent, but which is next adjacent to the proximal end stent. The stent graft 18 also includes at least one intermediate stent and preferably, as shown, a plurality of intermediate stents 122 which are provided on the graft 112 between the first and last covered stents 122', 120. The first and last covered stents and all the intermediate stents are covered, that is covered over their full longitudinal extent on at least one surface, with graft material.

As shown in FIG. 4, the stents may have a zig zag shape and are what is commonly known as Gianturco type stents or z-stents. The stents can be spaced on the graft 112 substantially equidistantly or with different distances between different sets of adjacent stents. In some embodiments, the stents can be provided in close proximity with minimal distances between adjacent stents. As shown, the stents are discrete, meaning separate, and not connected to each other except indirectly by way of the graft material.

The distal end stent 120 and the first covered stent 122' are internal stents whereas the intermediate stents 122 are external stents. However, whether particular stents are internal or external is not important and each stent can be either internal or external. By "internal stent" what is meant is that the stent is located on the internal surface of the graft and therefore has graft material on its outer side, whereas an "external stent" is located on the external surface of the graft and therefore has graft material on its inner side. However, it is preferable for the proximal end stent 122' and the distal end stent 120 are internal so as to present a smooth landing surface of the stent graft for graft to vessel apposition to ensure a tight interface. Each of the stents is attached to the graft 112, for example by sutures, although other attachment mechanisms are contemplated. FIG. 4 shows two intermediate stents 122. However, in other examples there can be other numbers of intermediate stents. Advantageously, there is at least one intermediate stent and preferably at least two intermediate stents as this is able to obtain particular advantages of a smooth deployment and possible repositioning before full deployment as described below.

Each of the stents of the stent graft is provided with a constraining mechanism for constraining the respective stent. However, in this embodiment, the constraining mechanisms for the proximal 122' and distal 120 end stents are not visible in the expanded state of FIG. 4. FIG. 4 shows the constraining mechanism 128 for each of the intermediate stents 122 is for constricting the respective stent. The constraining mechanism 124 for each of the intermediate stents is configured in a constricting configuration to constrict substantially the entire length and circumference of the respective stent, the length being in a longitudinal direction.

The constraining mechanism 128 for each of the intermediate stents 122 includes first and second constriction elements 126, 124. In the embodiment of FIG. 4, the first constriction element may be a first thread or filament 126 and the second constriction element may be a second thread or filament 128. Both the first and second threads/filaments may be made of suture material.

The first thread 126 is attached to and extends around substantially the entire circumference of a proximal section of the respective intermediate stent 122 whereby to constrict the proximal section of the respective intermediate stent when in a constricting configuration. The second thread 124 is attached to and extends around substantially the entire circumference of a distal section of the respective intermediate stent 122 whereby to constrict the distal section of the respective intermediate stent when in a constricting configuration.

In order to extend around the entire circumference of a stent section, the threads can pass radially internally of the struts of the stent, radially externally of the struts of the stent, or a mixture of radially internally and radially externally. In some embodiments, each thread may alternate around the circumference of the stent between passing radially internally and radially externally of the struts. For example, if the struts of the stents are considered to be numbered in a consecutive manner around the circumference of the stent, the first and second threads may pass around the inside of odd-numbered struts and the outside of even-numbered struts and thereby be threaded inside and outside the struts in an alternating manner around the circumference of the respective stent.

As shown in FIGS. 4 and 5, the first thread 126 extends about the circumference of the exterior of the graft at or near the proximal apices 123 and the second thread 124 extends about the circumference of the exterior of the graft at or near the distal apices 125 of intermediate stent 122. As shown at element 127, at one or more of the apices, the first and second threads 126, 124 extend through the graft material to the interior of the graft for a short distance. As shown in FIGS. 4 and 5, the first and second threads 126, 124 may extend around the circumference of the respective stent and be tied to each strut, or at least tied to a plurality of struts such as every second strut at or near the apices, 123, 125.

Each of the first and second threads 126, 124 forms a loop with a length which is substantially equal to an uncompressed circumference of the respective stent section, or at least which is not less than an uncompressed circumference of the respective stent section. However, in a fully constricted configuration each of the threads is restrained at a plurality of locations around its loop as described below in order to provide a constricting function and thereby to prevent the respective stent section from expanding to its full deployment diameter. Preferably, the first and second constriction elements, in this case the first and second threads 126, 124, are in a fully constricted configuration configured to constrain the respective stent section to a diameter of no more than half or more preferably no more than a third of its fully deployed diameter.

In FIG. 4, the constraining mechanism for the first covered stent 122' includes a single constriction element 130. The constriction element 130 corresponds to the first constriction element 126 of the intermediate stents 122. Like the constriction elements for the intermediate stents 122, the constriction element for the first covered stent 122' is positioned about the circumference of the stent and graft and weave in and out of the graft material at one or more apices, and in particular as shown in FIGS. 4 and 5 at one or more proximal apices 129 of the first covered stent 122'.

Figure 9:
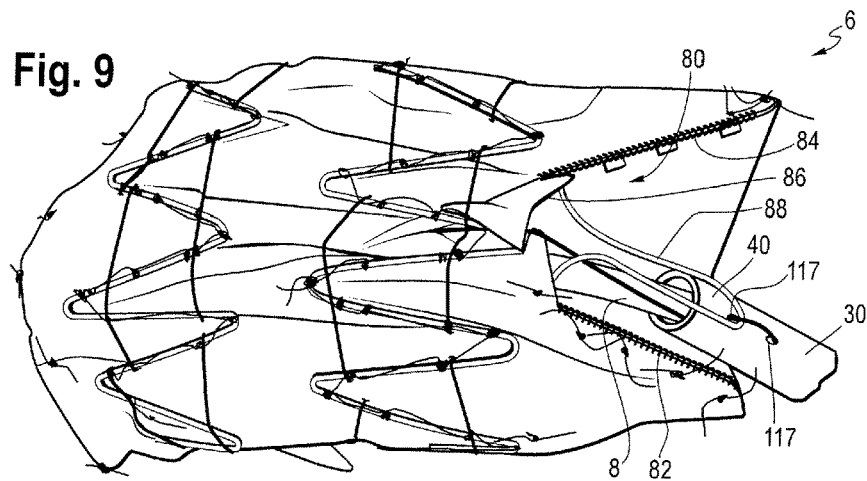
FIG. 9 is a partial view of the distal end of an exemplary stent graft showing the attachment of the distal end of the stent graft to the delivery device and a distal scallop in the graft material.
Figure 9A:
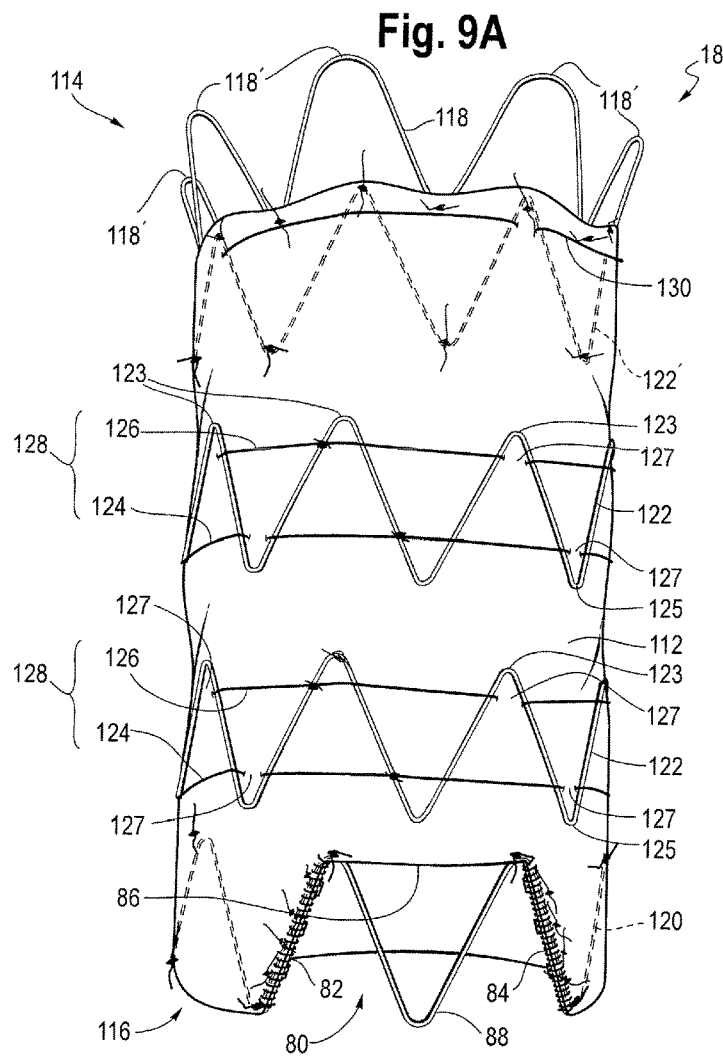
FIG. 9a is a view of the stent graft of FIG. 9 showing the distal scallop.

FIG. 9A shows another exemplary stent graft. The stent graft is identical to that shown in FIG. 4 except that it includes a scallop 80 or cut out at the distal end of the graft. The scallop 80 has two side edges 82, 84 and a lateral edge 86 extending between the two side edges 82, 84.

FIGS. 6-17 show how the constraining mechanisms of the first covered stent and the intermediate stents are held in a constricting configuration by the release wires until withdrawal of the release wires. FIGS. 6 to 17 also show the constraining mechanisms for the proximal and distal end stents.

Figure 6:
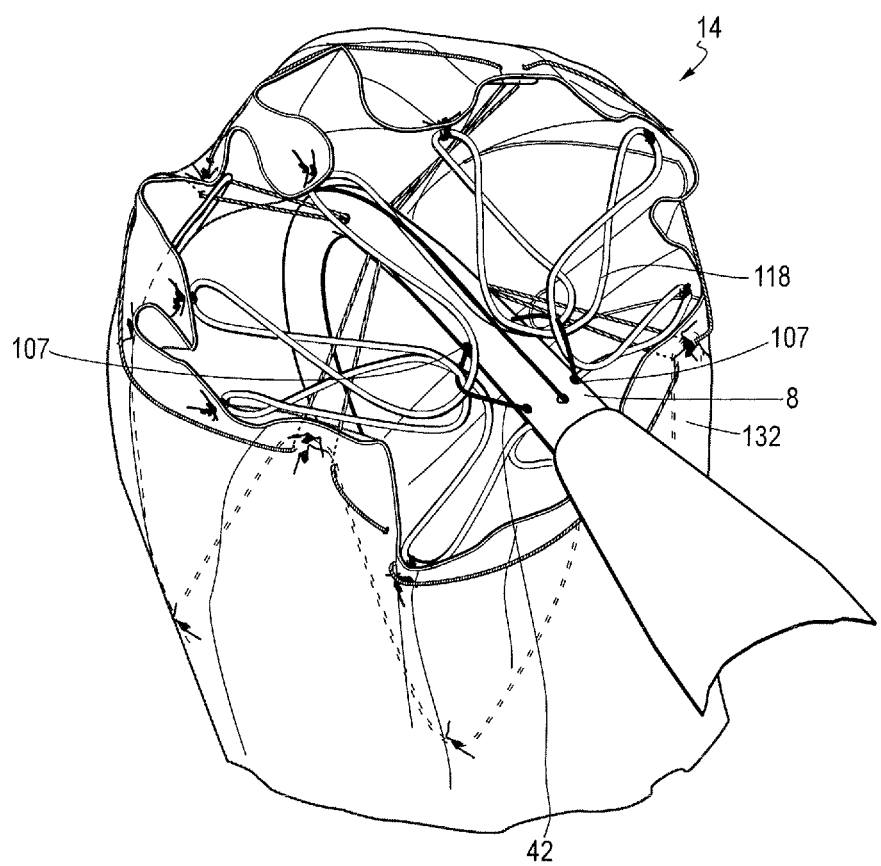
FIG. 6 is a partial view of the proximal end of the stent graft shown in FIG. 4 and, in particular, showing the attachment of the proximal end bare stent to a delivery device.
Figure 10:
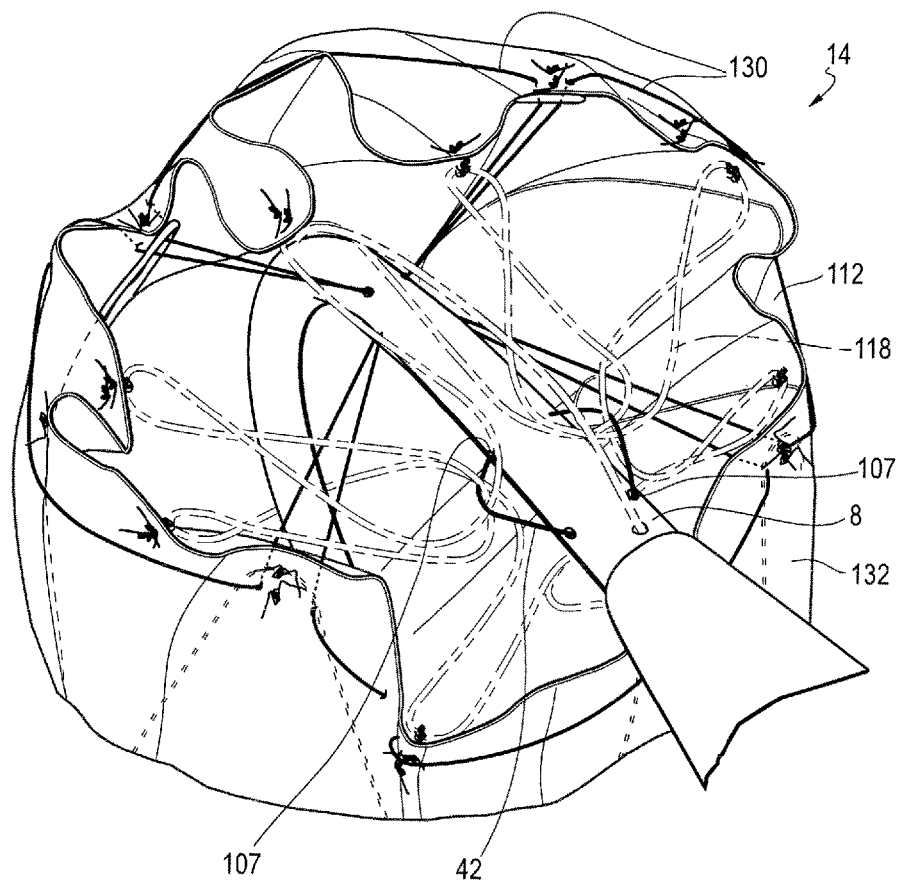
FIG. 10 is perspective partial view of the proximal end of the stent graft shown in FIG. 4 and, in particular, showing the attachment of the proximal end bare stent to a delivery device.

FIGS. 6 and 10 show the attachment of stent 118 (the proximal bare or uncovered stent) to the delivery device. As shown, the proximal apices 118a of the proximal stent engage one or more release (trigger) wires 42 that extend through an inner lumen (not shown) of the delivery device, exit from an aperture to engage the apices and then re-enters the delivery device. In one example, there are three release wires 42 which pass longitudinally through the lumen of the device and of the stent graft 18.

Figure 7:
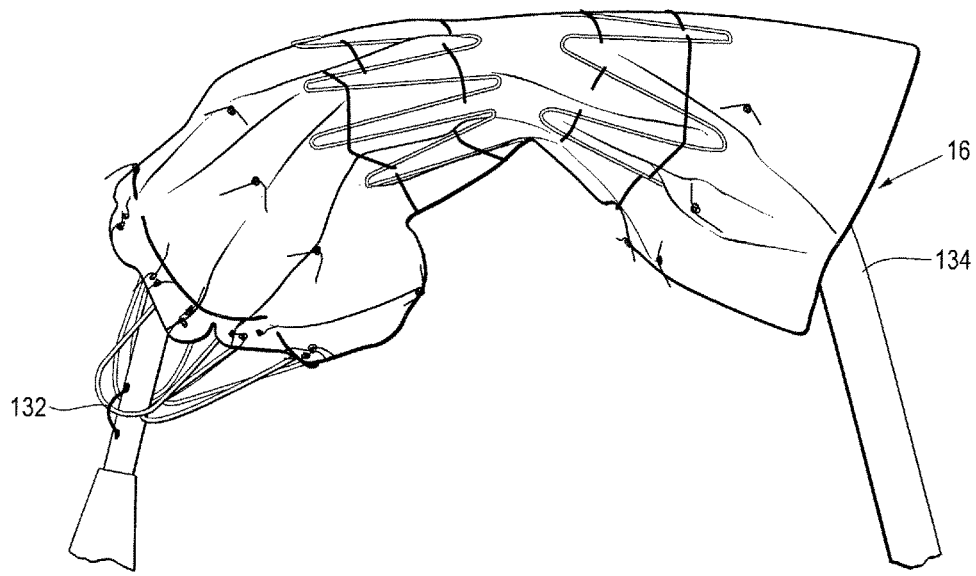
FIG. 7 is a side view of the stent graft of FIG. 4 disposed on a delivery device.

FIGS. 6 and 10 are perspective views from the proximal end of the medical device 18 when mounted on an introducer device and with all of the constraining mechanisms in a constraining configuration. FIG. 6, in particular, shows how the proximal end stent 118 is attached. FIG. 7 is a side view of the medical device 18 as loaded and constrained in the constraining configuration. As can be seen in FIGS. 6, 7 and 10, the proximal end stent 118 includes a constraining mechanism 132 at a proximal retaining or attachment region 14. At the constraining mechanism 132, each release wire has associated first and second apertures 107 in the release wire carrier 8. Each release wire 42 extends out of the release wire carrier 8 through its first associated aperture 107, passes over one or more of proximal apices 118' of the proximal end stent 118, and passes back into the release wire carrier 8 through its second associated aperture 107. In this embodiment, in which there are provided three release wires, each release wire at the proximal retaining section passes over and thereby constrains approximately one third of the proximal apices 118' of the proximal end stent 118. Although three release wires 42 are shown, a different number of release wires could be used, with each wire being attached to a different fraction of the proximal apices of the proximal end stent. In addition or alternatively, other means of attaching release wires to the proximal end stent as known in the art can be used. In some embodiments, one or more release wires play no role in the constraining mechanism 132.

Figure 8:
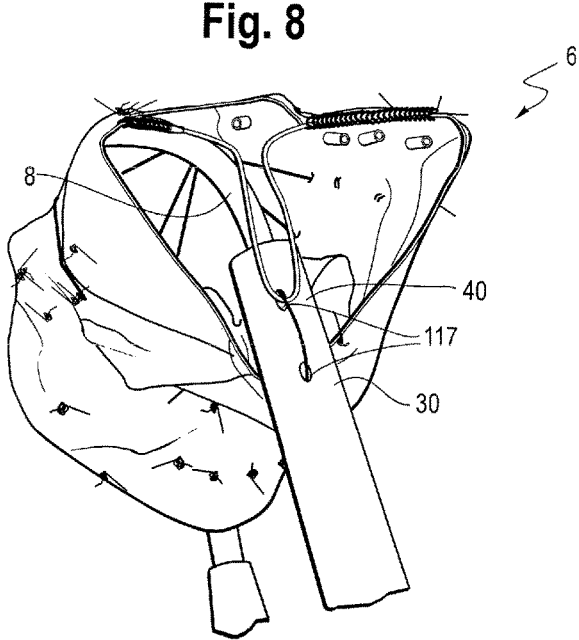
FIG. 8 is a partial view of the distal end of the stent graft of FIG. 4 showing the attachment of the distal end of the stent graft to the delivery device.

FIGS. 8 and 9 shows the attachment of the distal end stent 120 to the delivery device. The distal apices 120' of the distal end stent 120 are retained by release wires at a constraining mechanism 134 at the distal attachment region 16 as shown in FIGS. 8 and 9. As can be seen in particular from FIG. 8, in this embodiment the assembly 10' includes a pusher sheath or rod 30. At the constraining mechanism 134, the release wire carrier 8 and the pusher sheath 30 have sets of aligned apertures 117. There is a set of apertures 117 for each release wire. Each set of apertures 117 includes a first aperture in the release wire carrier 8 aligned with a first aperture in the pusher sheath and a second aperture in the release wire carrier aligned with a second aperture in the pusher sheath. The apertures in the release wire carrier are not visible in FIG. 8 since they are within the pusher sheath 30.

Each release wire 42 extends from the release wire carrier 8 out of its respective first apertures to the outside of the pusher sheath 30. The release wire passes over one or more distal apices 120' of the distal end stent 120 on the outside of the pusher sheath 30 and then extends back into the release wire carrier through the respective second apertures. The release wires 42 for the distal end stent 120 may be the same s or different release wires from the release wires 42 for the proximal end stent 118. The constraining mechanism 134 constrains the distal end stent 120 on the pusher sheath 30. This is advantageous as it can assist the pusher sheath with advancing the stent graft. In other embodiments, the sets of apertures 117 can be provided just in the release wire carrier and not in the pusher sheath so that the pusher sheath is not directly attached to the distal end stent.

One or more or all release wires 42 can each hold a plurality of distal apices 120' of the distal end stent 120. In one embodiment, all of the distal apices 120' of the distal end stent 120 are restrained by a release wire. In other embodiments, other means of constraining the distal apices of the distal end stent can be used.

Thus, the proximal apices 118' of the proximal end stent 118 and the distal apices 120' of the distal end stent 120 can be coupled to the release wires such that the release wires can be withdrawn so as to release the apices. Other possible techniques for providing constraining mechanisms for the proximal and distal end stents are disclosed in WO 2006/037086, which is incorporated herein by reference in its entirety.

As shown in FIGS. 9 and 9A there may be a scallop or cut out 80 at the distal end 116 of the medical device 18. The scallop 80 may be of the configurations shown in the figures and described in the accompanying text of U.S. Pat. No. 7,413,573 to Hartley et al., incorporated by reference herein. The scallop may be disposed between an adjacent pair of struts of the distal end stent 120 with no struts crossing the scallop or it may be disposed between a pair of struts with one or more struts 88 between the pair of struts crossing the scallop. The periphery of the scallop may be partially stitched to one or more struts disposed along the periphery of the scallop. The scallop is designed and configured to align with one of the arteries of the arch (as shown in FIG. 1), such as the innominate artery, so as to not block that artery. The actuation mechanism coupling closest to the scallop 80 may be a coupling to the release wire or rod which during withdrawal has the proximal-most distal end of the release wires or rods that actuate the distal end of the stent graft. This can enable the part of the second end of the stent graft which includes the scallop to expand before other parts of the second end of the stent graft.

FIGS. 10 to 17 show more clearly how the construction elements of the constraining mechanisms of the first covered stent and the intermediate stents are coupled to the release wires. FIG. 10 is a view of the assembly of FIG. 6 but showing more clearly the constriction element 130 of the first covered stent 122'.

As can be seen in FIG. 10, the thread of the constriction element 130 passes around an outer surface of the graft 112 where it is attached to the first covered stent 122'. As shown, the thread 130 is continuous around the full circumference of a proximal section of the first covered stent 118, adjacent to the proximal end 114 of the graft. In this embodiment, the thread 130 is tied to the first covered stent.

Figure 11:
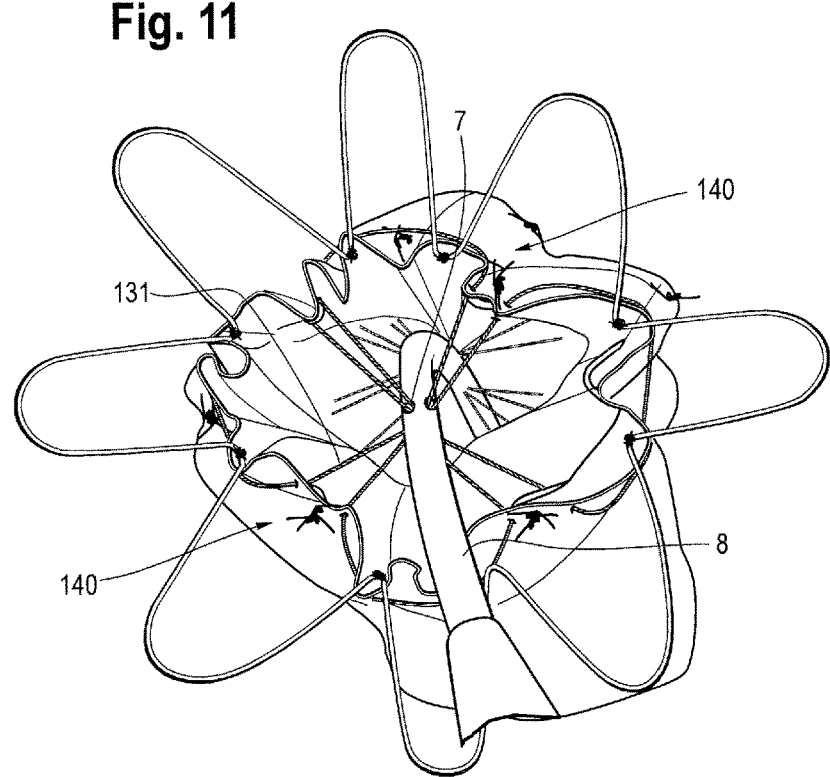
FIG. 11 is another perspective partial view of the proximal end of the stent graft shown in FIG. 4 and, in particular, showing release of the proximal end bare stent from the delivery device.
Figure 12:
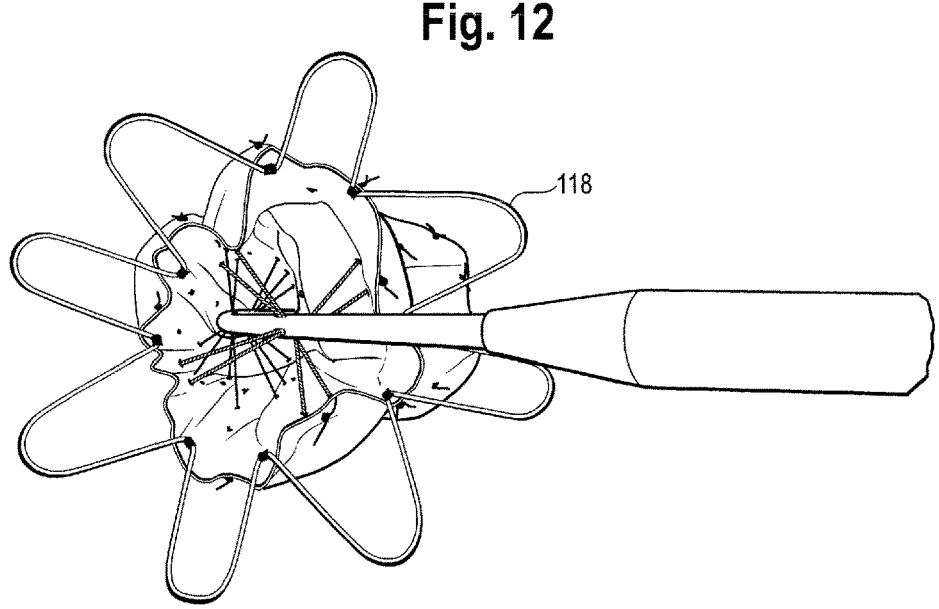
FIG. 12 is another perspective partial view of the proximal end of the stent graft shown in FIG. 4 and, in particular, showing release of the proximal end bare stent from the delivery device.

FIGS. 11 and 12 show the assembly of FIGS. 6 to 10 but in which the proximal end stent 118 has been released from the retaining section 132. As shown in FIG. 11, at several restraining locations 140 around the circumference of the graft, the thread 130 passes through the graft to the interior of the graft, is passed around one or more of the release wires 42, and passes back out of the graft to the exterior of the graft. In other words, at each restraining location, a bight 131 of the thread is restrained by one or more release wires 42. As further shown in FIG. 11, for each release wire 42, there is provided an aperture 7 associated with the thread 130 in the release wire carrier 8, in this case longitudinally aligned with the thread 130, which exposes the respective release wire. In some embodiments, the release wire can extend out of and back into its respective aperture to form an arc or loop. In other embodiments, the aperture can be in the form of first and second apertures, like that shown for the proximal end stent release wires, allowing the respective release wire to extend out through a first aperture and back in through a second aperture in a similar manner to the apertures 107 described above. In other embodiments, the release wires do not extend through the apertures but are simply exposed within the release wire carrier 8 by the apertures 7.

At each of the restraining locations 140, a bight 131 of the thread 130 passes around one or more release wires. The thread is thereby restrained by the release wires at the restraining locations, constricting the diameter of the proximal section of the first covered stent. As can be seen in FIG. 11, in this embodiment, at each restraining location 140, the thread 130 passes through the graft at points either side of a strut of the first covered stent in the vicinity of a proximal apex 120' thereof. Accordingly, if the bight 131 of thread at each restraining location can be considered to include a first length on one side of its coupling to the release wires and a second length on the other side of its coupling to the release wires, the first length passes through a proximal apex of the first covered stent and the second length passes through the graft adjacent to that proximal apex. The thread 130 may be attached directly to the first covered stent at or adjacent to the points at which it passes through the graft.

However, the thread does not need to pass through the graft in the vicinity of apices in all embodiments but can pass through the graft at any points. In some embodiments, at each restraining location the thread is attached to a first point of a first strut where it passes through the graft into the interior of the graft and is attached to a second point of a second strut where it passes through the graft out of the interior of the graft. The first and second points are points on adjacent struts either side of and close to an apex. In this way, the struts can act to hide or shield the thread from any other medical device or components inside the graft.

While the release wires 42 are present, the thread 130 is held in a constricting configuration, thereby constricting the proximal end of the first (proximal) covered stent 122'. However, as the release wires 42 are withdrawn from the restraining locations, the thread 130 is released from the constricting configuration condition and allows the proximal section of the first covered stent 122' to expand beyond its constricted diameter.

In the embodiment shown in FIG. 11, there are three release wires and four restraining locations for the thread 130 and therefore four bights 131 of thread. Two of the release wires constrain one bight 131 of the thread 130 each. One of the release wires constrains two bights 131 of the thread 130. However, as mentioned above, the number of release wires may vary. In some embodiments, there may be 6 or 7 release wires. The number of bights of threads and restraining locations also may vary. It is possible to have any number of release wires and any number of bights of thread. In one embodiment, there are 6 bights 131 of the thread. If there is the same number of bights as release wires, each release wire can restrain one bight of the thread, although it is not always necessary for every release wire to restrain a bight 131 of the thread. In some embodiments, especially if there are more bights of the thread than release wires, one or more release wires may restrain more than one bight of the thread.

In the embodiment of FIG. 11 and as shown in later figures, when the release wires are pulled, because they are of varying lengths, the bights will be release separately and hence sequentially to sequentially circumferentially expand the restrained stent. In other words, one portion of the stent will expand first and then the remaining portions of the stent will expand, one after the other in a sequential fashion.

The number of bights of the thread and the number of release wires may depend on the size of the stent graft and the number of apices on a stent. For example, for a 42 mm stent graft, there may be 8 bights of the thread. However, in many situations, it has been found that 4 bights of the thread works well.

In addition, the number of apertures 7 associated with the thread 130 is not important. Each release wire can have a dedicated aperture associated with the thread 130, or a single aperture may expose more than one release wire for coupling to the thread.

The release wires may be of the same length and independently operable, that is, they can be withdrawn in a staggered fashion so as to release different parts of the constraining mechanism at different times. This can be achieved by coupling them to their own dedicated actuation sections 50 as shown in FIGS. 2 and 3. However, as set forth above, the release wires are different lengths and designed to be withdrawn together so as to release different parts of the constraining mechanism at different times, and hence different sides of the graft at different time.

Releasing different parts of the constraining mechanism at different times, thereby expanding the circumference of the graft constrained by the constraining method sequentially around its circumference allows the proximal section of the first covered stent to expand beyond its constricted diameter to its uncompressed or fully deployed diameter in stages. This permits the proximal end of the stent to conform to the curved vessel with no gaps between the vessel wall and the graft end. In practice, the release wires are typically designed to be withdrawn so that there is only a very short interval between the release of different parts of each constrained stent section, and there is only a short interval between the release of adjacent stent sections. The release wires are preferably configured to be withdrawn so that each constrained stent is completely released from the release wires before any part of the next constrained stent in the direction of withdrawal is released from the release wires. Hence, in practice, the first stent is released in stages around its circumference first, then the next stent is released around its circumference and so on. With the intermediate stents having constraining mechanisms at the proximal and distal apices, the proximal end of the first intermediate stent may be released circumferentially in stages, followed by the distal end being released circumferentially in stages, followed by release of the proximal end of the next immediate stent in circumferential stages, followed by release of the distal end of the next immediate stent is circumferential stages, and so on depending on the number of intermediate stents. However, the circumferential and longitudinal release of the proximal and distal ends of each intermediate stent may be at substantially the same time.

Because the thread has a length substantially equal to an uncompressed circumference of the respective stent section, once the stent section has expanded to its uncompressed diameter, the thread 130 forms a loop substantially corresponding to the expanded circumference of the stent section.

In the embodiments shown, the restraining locations and therefore the bights of thread are at regular angular intervals around the proximal section of the first covered stent in order to provide an even constricting effect. However, in other embodiments the restraining locations and bights of thread may not be at regular angular intervals.

Furthermore, the thread 130 does not in all embodiments need to be generally external to the graft provided that it is disposed with respect to the first covered stent so as to be able to constrict the proximal section of the first covered stent when restrained at the restraining locations. Therefore, the bights are not in all embodiments associated with points at which the thread passes through the graft; the thread may in some embodiments already be internal to the graft, especially if the stent is an internal stent. Each bight can be a length of the thread, from a first point of attachment of the thread to the graft and/or stent, to a second point of attachment to the graft and/or stent, wherein the bight passes around one or more of the release wires between the first and second points of attachment.

Each of the threads of the constraining mechanisms of the intermediate stents can be attached to the release wires in a corresponding manner.

Figure 13:
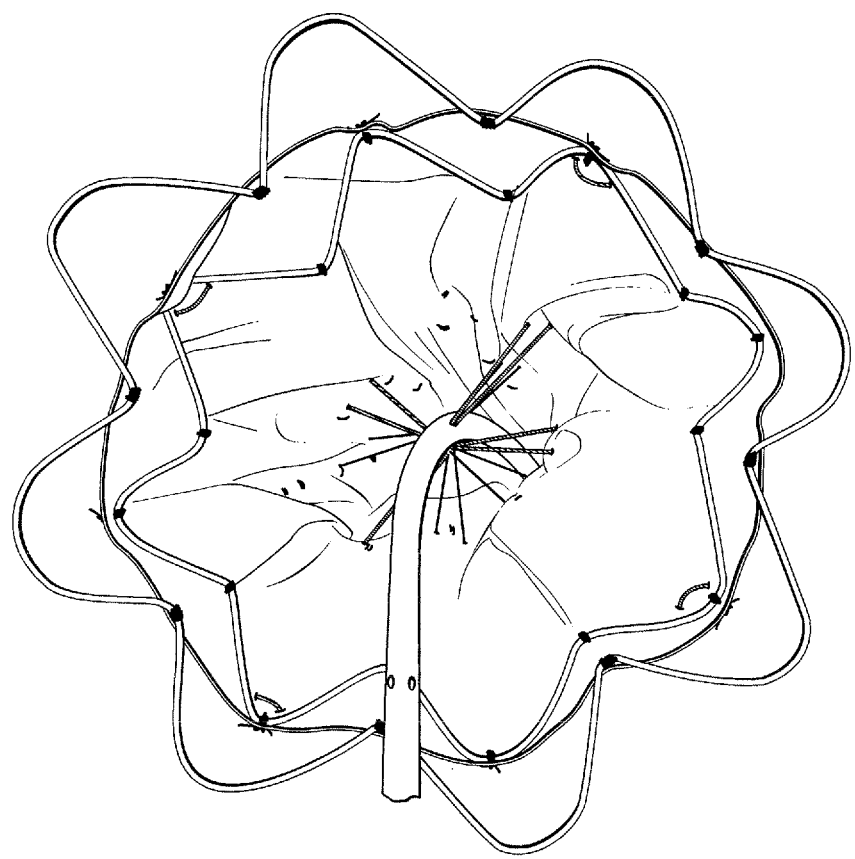
FIG. 13 is a partial end view of the proximal end of the stent graft shown in FIG. 4 and, in particular, showing an internal view of a stent/delivery system attachment mechanism.
Figure 14:
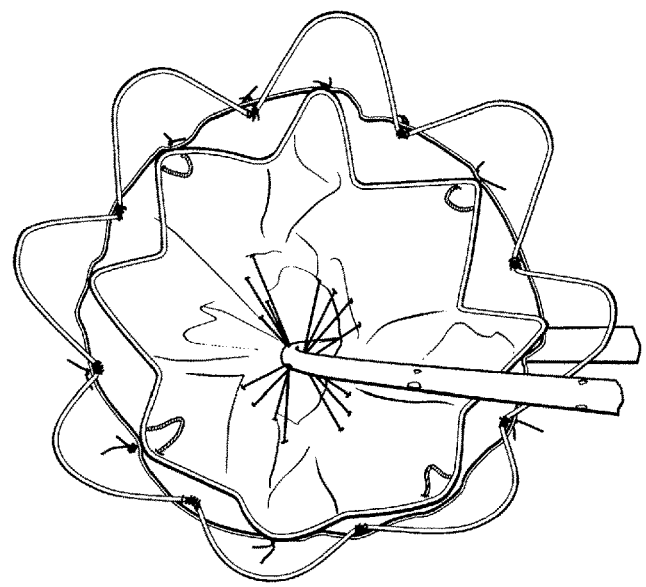
FIG. 14 is another end view of the proximal end of the stent graft shown in FIG. 4 and, in particular, showing an internal view of a stent/delivery system attachment mechanism.
Figure 15:
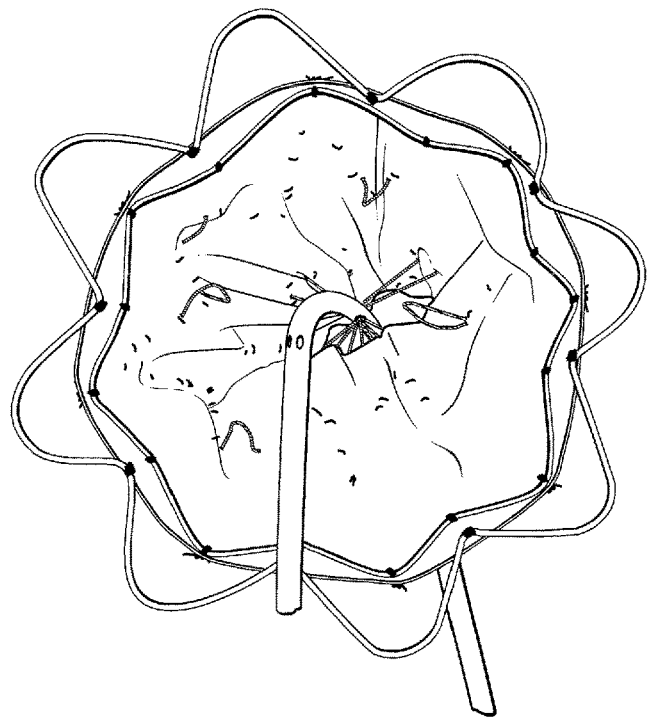
FIG. 15 is an up close partial end on view of the interior of the proximal end portion of the stent graft of FIG. 4.
Figure 16:
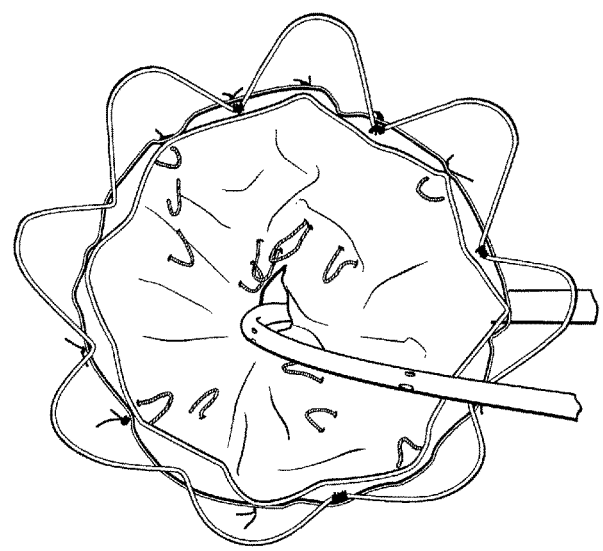
FIG. 16 is an end on view of the proximal end of the stent graft of FIG. 4 and, in particular, showing the bare stent, the proximal most stent and a portion of the next adjacent stent released from the delivery device.

For example, FIGS. 13 and 14 show the assembly of FIG. 6 but in which the constraining mechanism 130 of the first covered stent has been released. FIG. 13 shows more clearly the constraining mechanism of the intermediate stent 122 adjacent to and distal of the first covered stent 122'. FIGS. 15 and 16 show the assembly of FIG. 6 but in which the constraining mechanisms 130, 124 of the first covered stent and the intermediate stent adjacent to and distal of first covered stent have been released. FIG. 15 shows more clearly the constraining mechanism of the intermediate stent 122 which is distal of the first covered stent 122' and separated therefrom by one stent.

As can be seen from FIGS. 6 to 16, the constraining mechanisms of the stents of the stent graft are coupled or include couplings to the release wires in the same order along the release wires from the proximal end to the distal end of the stent graft as the order from the proximal end to the distal end of the stent graft of the stent sections that they constrain. This means that withdrawal of the release wires in a direction away from the heart releases those stent sections in order from the proximal to the distal end of the stent graft.

FIG. 17 shows a longitudinal cross-section through a part of the assembly 10' in the region of an intermediate stent 122. FIG. 17 does not show the stent 122 itself as only the internal surface of the graft 112 is visible in FIG. 11 whereas the stent 122 is an external stent. The bights of the threads 126, 128 can only be seen for the sections that are internal to the graft 112.

As shown in FIG. 17 and as discussed above, in the region of the medical device 18, the deployment assembly 10' has, in this embodiment, a guide wire carrier 24 and a release wire carrier 8 (typically the carrier of the introducer for carrying the medical device) located coaxially around the guide wire carrier 24, such that the guide wire carrier resides in a lumen of the carrier 8. In some embodiments the guide wire may be located directly in the release wire carrier 8 thus avoiding the need for a separate guide wire carrier 24.

The release wires 42 pass along the annular space between the guide wire carrier 24 and the release wire carrier 8. For each thread 126, 128, each release wire is exposed by an aperture 7 in the release wire carrier 8. At each of the apertures 7, one of the release wires exits through the aperture 7, where at least one bight passes around it. The release wire then re-enters the annular space between the guide wire carrier and the release wire carrier. However, the apertures 7, release wires and bights can be configured in other fashions such as discussed above for the first covered stent.

The release wires eventually pass into the nose cone dilator 20 at the distal end of the assembly to be secured thereby. A guide wire passes through the lumen of the guide wire carrier, catheter or cannula 24 in conventional manner. The apertures 7 and/or the restraining locations associated with each thread 126, 128 may be equally spaced around the release wire carrier. In this embodiment, the apertures are spaced at approximately 120° to each other and the restraining locations are spaced at approximately 90° to each other. However, as discussed above, the number of restraining locations and release wires may vary.

The assembly is operated as described below, with reference to FIGS. 6 to 16 and 18 to 26. The device 18 is compressed in the sheath 32 with all of the constraining mechanisms in a constraining configuration. The figures show the sheath as withdrawn from over the device, but one of skill in the art would recognized that device 18 had been constrained therein prior to withdrawal of the sheath.

The stent graft 18 is advanced in a known manner to a deployment site, in this example being the ascending aorta of a patient. It is to be noted that FIGS. 18-26 show an experimental mock up with a tube designed to imitate the aorta of a patient and in particular the ascending aorta just downstream of the heart and the heart valve 1. The region designed to imitate the ascending aorta of a patient is labelled 1'.

Figure 18:
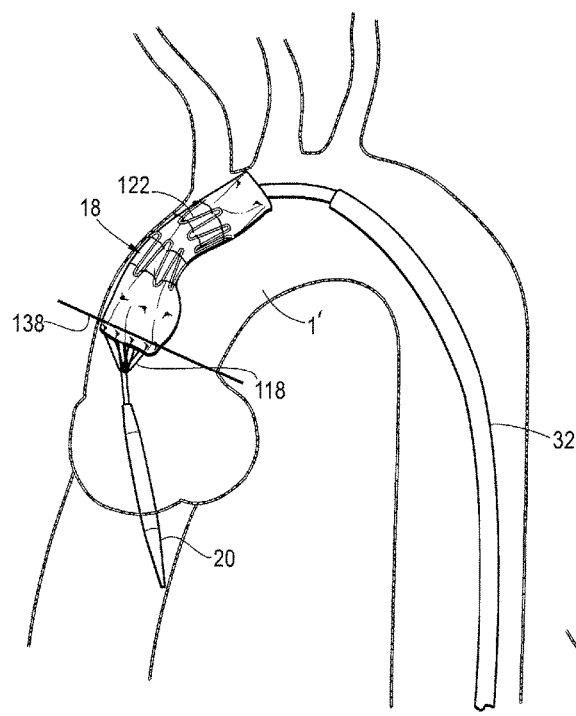
FIGS. 18 through 26a are side views of the sequential deployment of the stent graft of FIG. 4 in an ascending aorta at various sequential stages of deployment.

Once the stent graft is located in approximately the correct position, the sheath is withdrawn in a known manner leaving the situation shown in FIG. 18. This corresponds to the stent graft being in the configuration shown in FIGS. 6 and 7.

Owing to the constriction elements constricting the intermediate stents 122, the constriction element 130 constricting the first covered stent 122', and the constraining mechanisms at the proximal and distal retaining sections, the stent graft 18 is partially expanded but has not fully deployed in FIG. 18 despite the withdrawal of the sheath. In particular, the constraining mechanisms constrain the stents to no more than half or no more than a third of their unconstrained and fully deployed diameter. This enables the stent graft to be imaged and easily repositioned if it is in the incorrect location. In particular, if the stent graft is fully deployed immediately after withdrawal of the sheath, repositioning can be difficult as the stent graft will be pressing on the walls of the vessel. By keeping the stent graft constrained even after the sheath has been withdrawn, readjustment is made easier. This also is critical to the placement of a scallop so that the arch artery adjacent the distal end of the stent graft is not blocked by the graft material.

In FIGS. 18-26a, a line 138 is shown which marks a substantially perpendicular direction with respect to the ascending aorta and identifies a position which should be taken by the first covered stent when deployed. In the one embodiment, the release wires 42 are the same length and withdrawn in a staggered fashion. For example, the release wires can be withdrawn concurrently but staggered so that during withdrawal each release wire is at a different stage in its withdrawal process. However, as discussed above, the release wires may in other embodiments be different lengths and withdrawn together.

Nevertheless, in any of these situations, the release wires are preferably withdrawn so as to completely release each constrained stent from the release wires in a circumferentially staged manner before any part of the next constrained stent in the direction of withdrawal is released from the release wires. This is to ensure that the constrained stents are released in sequence from the proximal end to the distal end of the stent graft.

Figure 19:
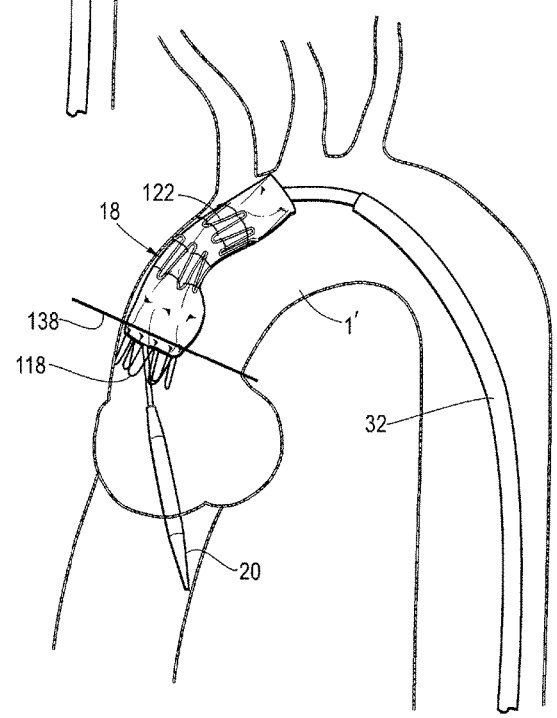
Figure 20:
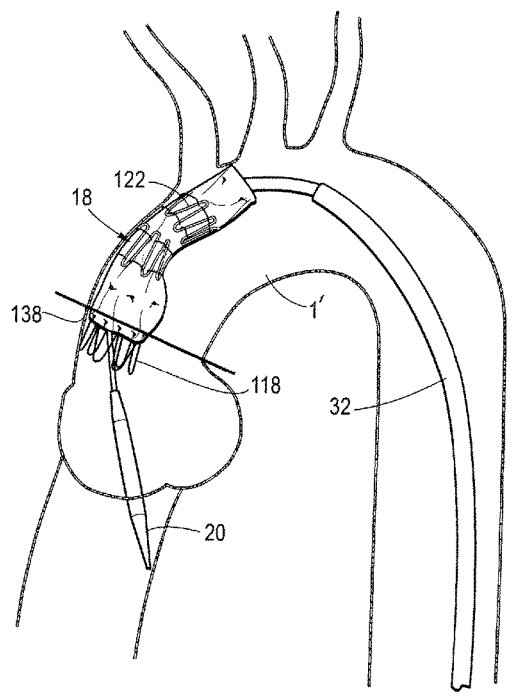
Figure 21:
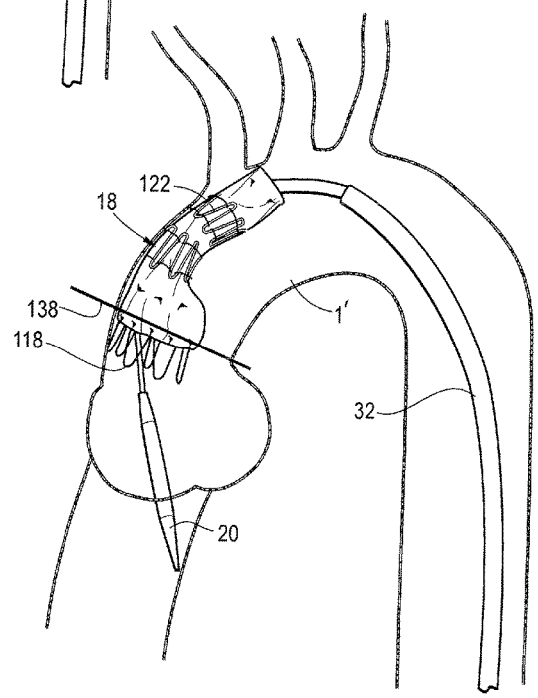

As the release wires are of (in other words closer to the operator than) the points at which they are coupled to the proximal apices of the proximal end stent, the proximal apices 118' of the proximal end stent 118 are no longer constrained and can spring open as shown in FIG. 19.

Because of the staggered nature of the withdrawal of the release wires in this embodiment, the apices 118' of the proximal end stent 118 are released and spring open in stages, as shown in FIGS. 27 to 30, allowing a gradual expansion process. This situation after all of the proximal apices 118' of the proximal end stent 118 have been released can be seen in FIGS. 11 and 19.

In the embodiments shown, the release wires are withdrawn proximally of (in other words closer to the operator than) the bights 131 of the thread of the constriction element 130 of the proximal apices of the first covered stent 122' are released and the constriction element 130 of the proximal apices of the first covered stent no longer provides a constricting function and the proximal end of the first covered stent can spring open. Because of the staggered nature of the withdrawal of the release wires in this embodiment, the bights 131 of the thread of the constriction element 130 of the first covered stent are released in stages, as shown in FIGS. 31 to 34, allowing a gradual expansion process for the proximal section of the first covered stent 122'.

Figure 22:
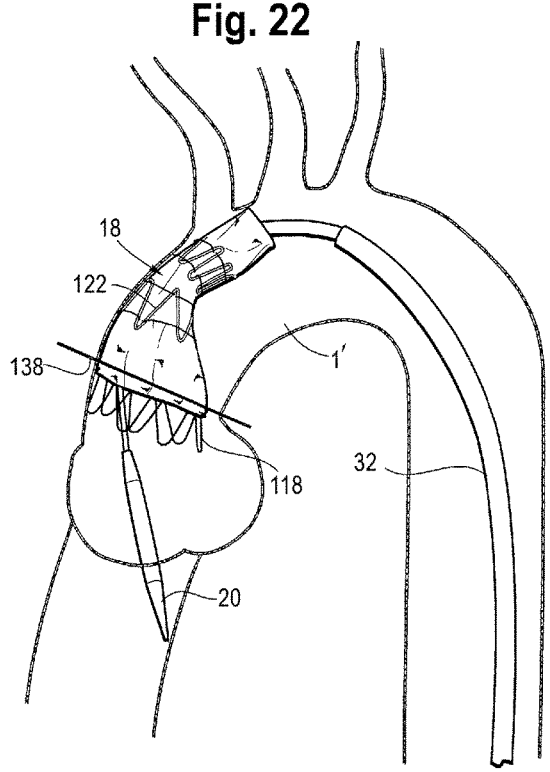
Figure 23:
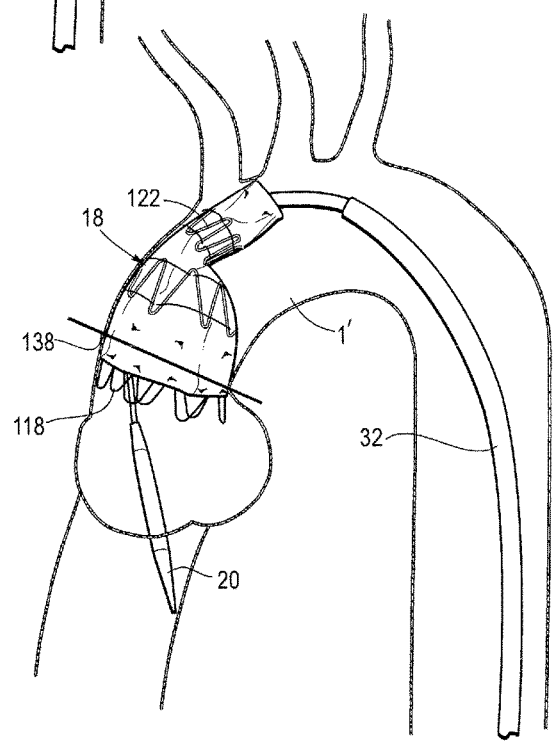

FIGS. 13 and 22 show the position after the constriction element of the first covered stent has been released. As can be seen in FIG. 22, the first covered stent has begun to expand towards its fully deployed diameter. However, because of the constriction elements constricting the intermediate stents, the proximal end stent 118 is unable to completely fully deploy.

As the release wires 42 are further withdrawn proximally of (in other words closer to the operator than) the bights of the constriction elements of the first intermediate stent 122 distal end and the constriction elements of the first intermediate stent distal end are released and therefore provide no more constricting function of the stent distal end, and the first intermediate stent can expand towards its full deployed diameter. Because of the staggered nature of the withdrawal of the release wires in this embodiment, the bights of the threads of the constriction elements of the first intermediate stent are released in stages, as shown in FIGS. 35 to 40, allowing a gradual expansion process for the first intermediate stent both circumferentially and longitudinally.

Figure 30:
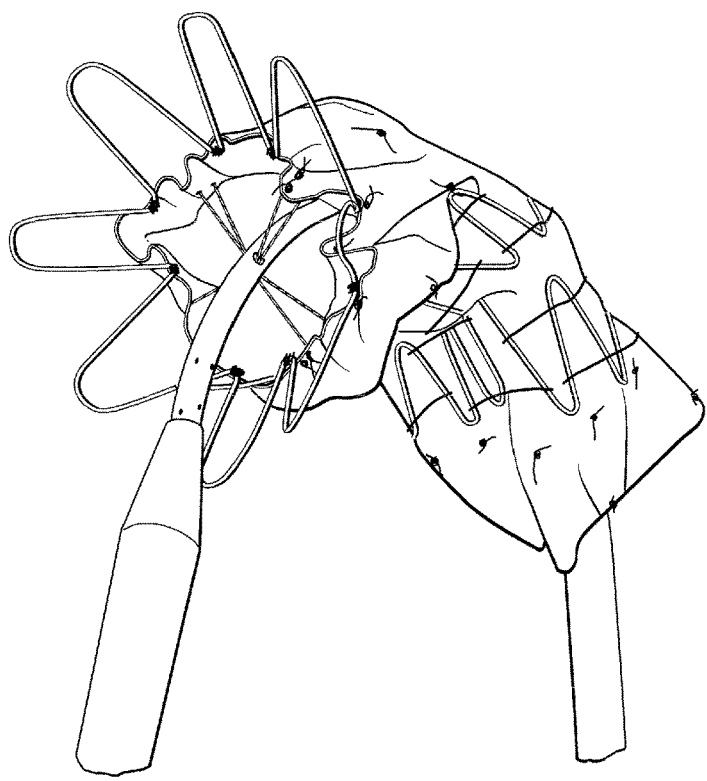
Figure 31:
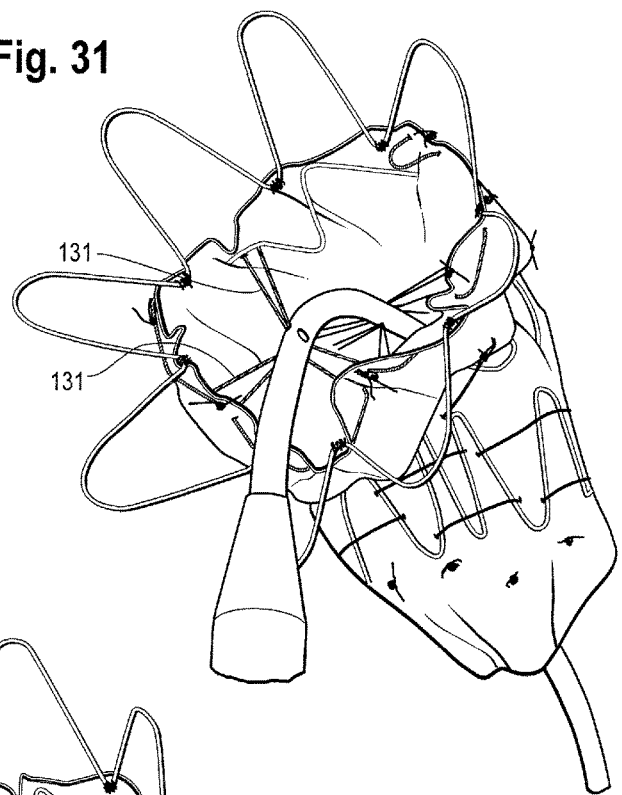
Figure 32:
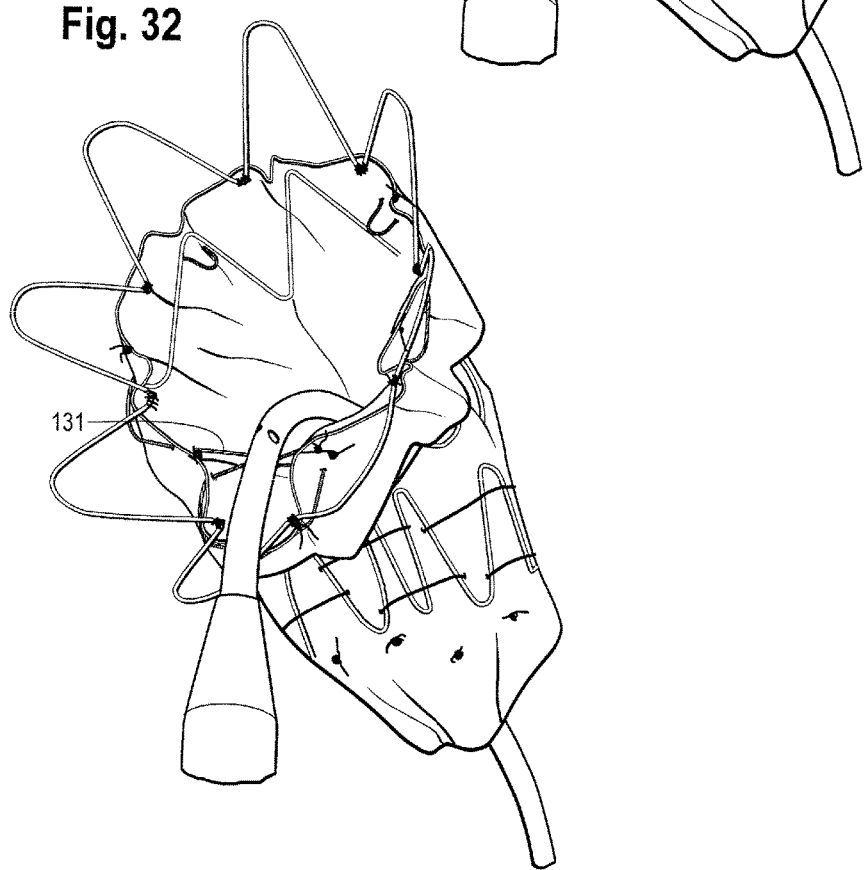
Figure 33:
Figure 34:
Figure 35:
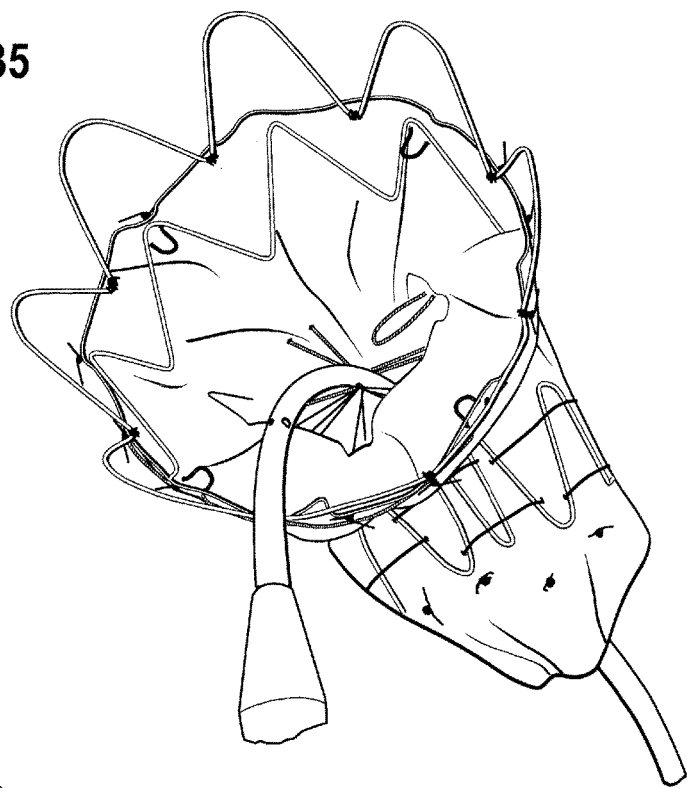
Figure 36:
Figure 37:
Figure 38:
Figure 39:
Figure 40:

As shown in FIGS. 35 to 40, each release wire is withdrawn in sequence from the bights by which it is coupled to the constraining mechanism. The bights of this constraining mechanism can be considered to be arranged in sets, with each release wire being coupled to a set of bights of the constraining mechanism. A set of bights for a particular release wire includes any bights of the thread 126 of the first constriction element to which it is coupled as well as any bights of the thread 128 of the second constriction element to which it is coupled. Each set of bights is released from its respective release wire in turn so that all bights of a given set are released before any bights from the next set to be released. In this way, the constraining mechanism 124 as a whole is gradually released, allowing the first intermediate stent to expand. The first constriction element 126 can be entirely released before any bights of the second constriction element 128 are released. Referring to FIGS. 30 to 40, the process of release of the stents is as follows. As shown in FIG. 30, the proximal end of the first covered stent 118 is constrained to the delivery device. FIG. 31 shows one circumferential section released as a release wire is pulled. FIG. 32 shows the next circumferential section released. FIG. 33 shows the next circumferential section released, and FIG. 34 shows the last circumferential section released such that the first covered stent is completely released.

As the release wires are further withdrawn, referring to FIGS. 35 to 40, the proximal end of the first intermediate stent is sequentially circumferentially released in the same manner as the first covered stent. Thereafter, as the release wires are further withdrawn, the distal end of the first covered stent is sequentially circumferentially released. Thereafter, the second intermediate and any subsequent intermediate stent is released in the same manner. Although in the shown embodiments the intermediate stents have two constraining mechanisms, the intermediate stents may be provided each with only one constraining mechanism that is circumferentially released.

Figure 24:
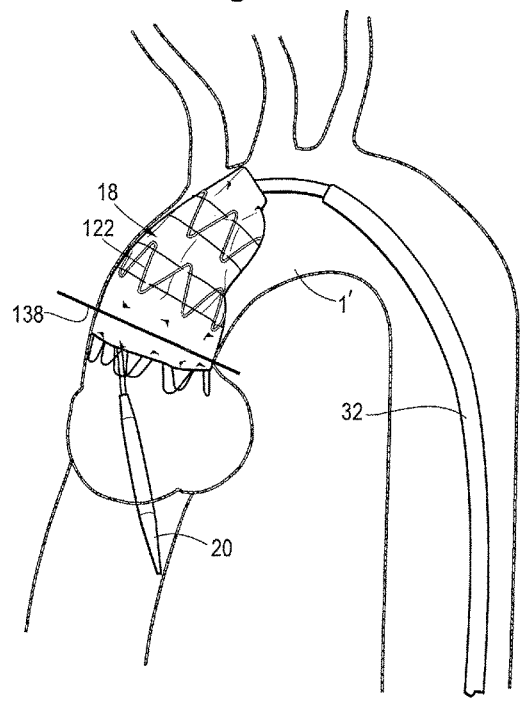

FIGS. 15 and 24 show the position after the release wires 42 have been withdrawn proximally of (in other words closer to the operator than) the bights of the constriction elements of the first intermediate stent 122. The constriction elements of the first intermediate stent at this stage provide no more constricting function, and the first intermediate stent can expand towards its full deployed diameter. This in turn allows the proximal end stent 118 to expand further. As can be seen in FIG. 24, the first covered stent also at this point moves closer towards the line 138.

Figure 25:
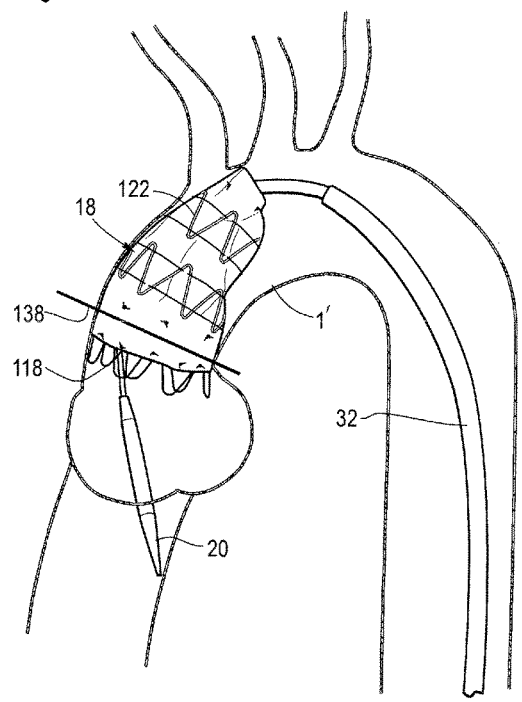
Figure 26:
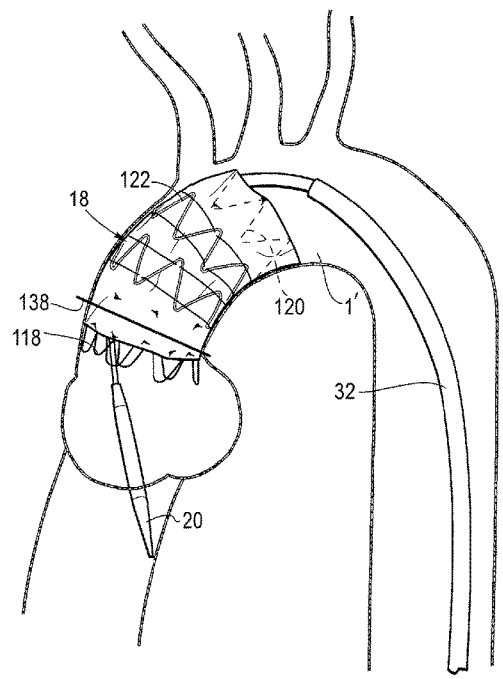
Figure 26A:
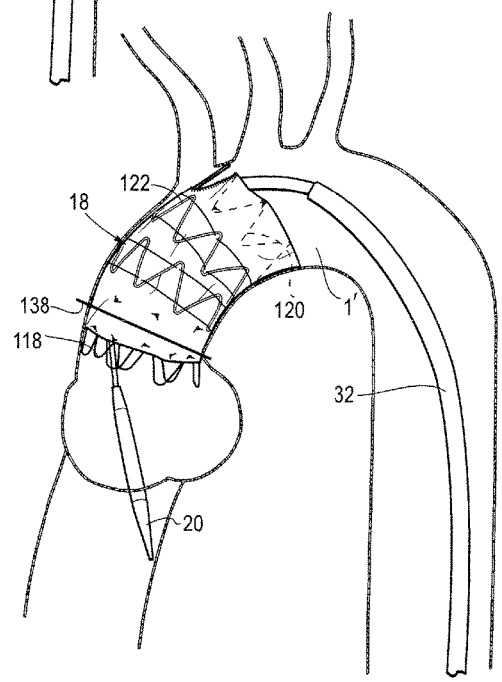
Figure 27:
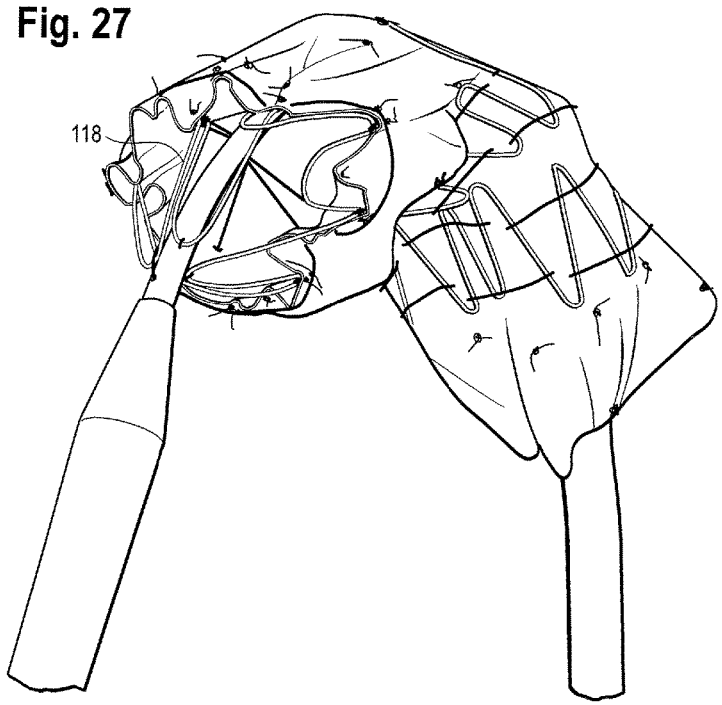
FIGS. 27 through 43 are perspective views of the sequential deployment of the stent graft of FIG. 4 at various sequential stages of deployment.
Figure 28:
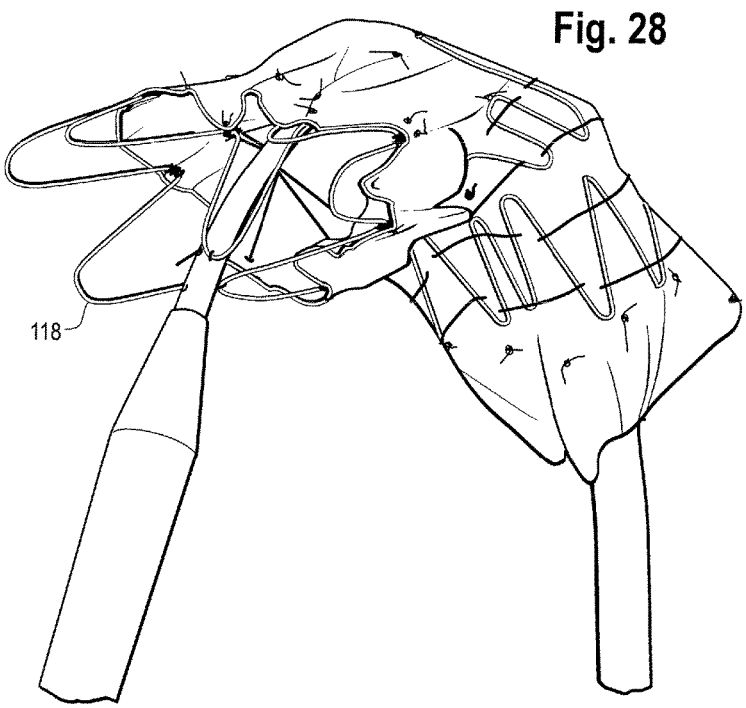
Figure 29:
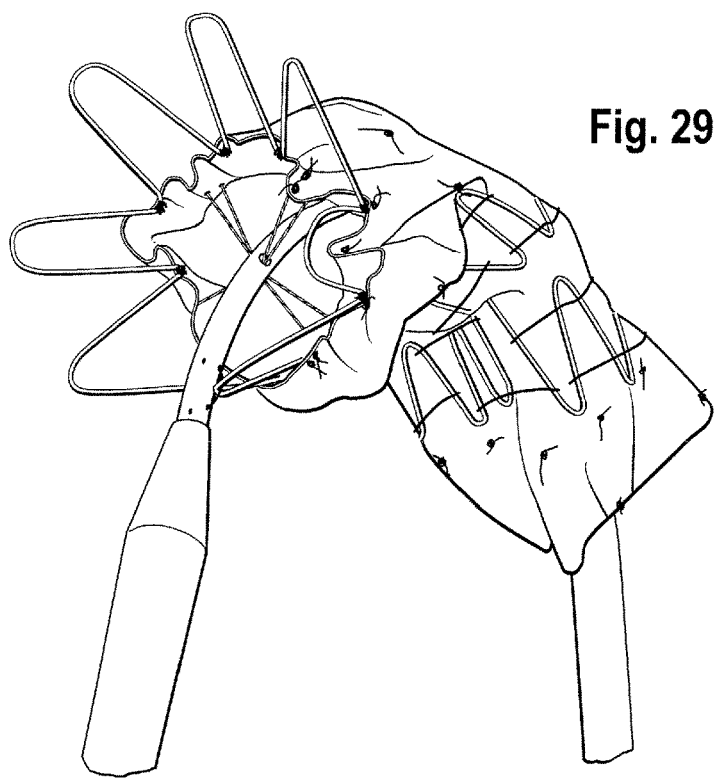

As can be seen from FIGS. 25 to 26a, further withdrawal of the release wires 42 causes each of the stents in turn from the proximal to the distal end of the stent graft gradually to expand in a smooth manner. FIG. 26a shows the stent graft as fully deployed.

Figure 41:
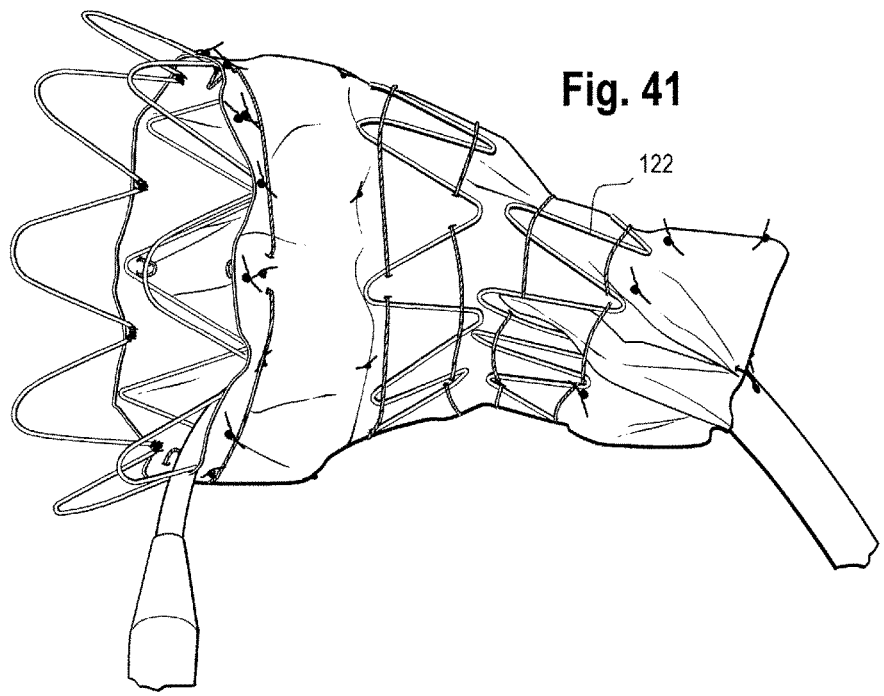
Figure 42:
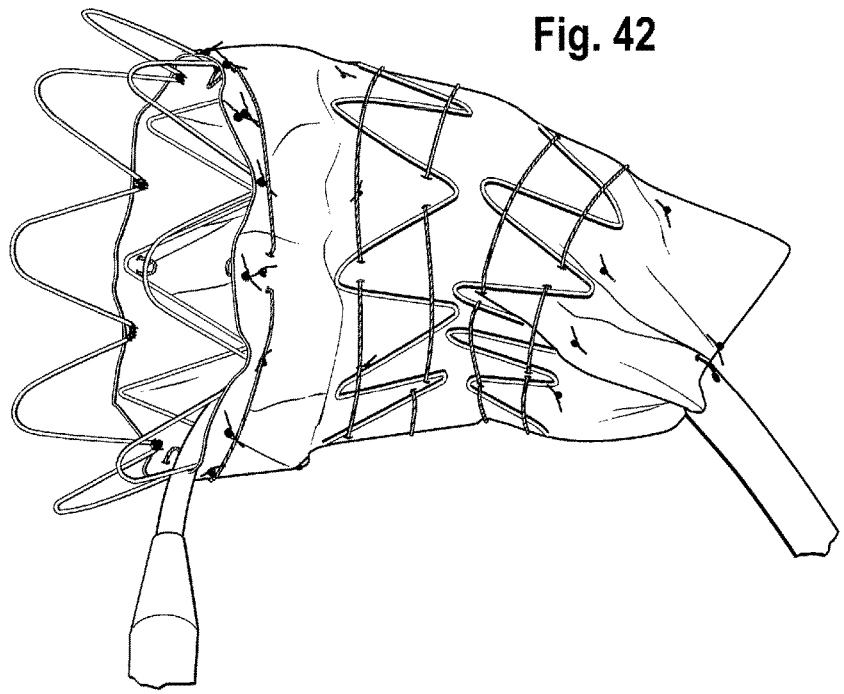
Figure 43:
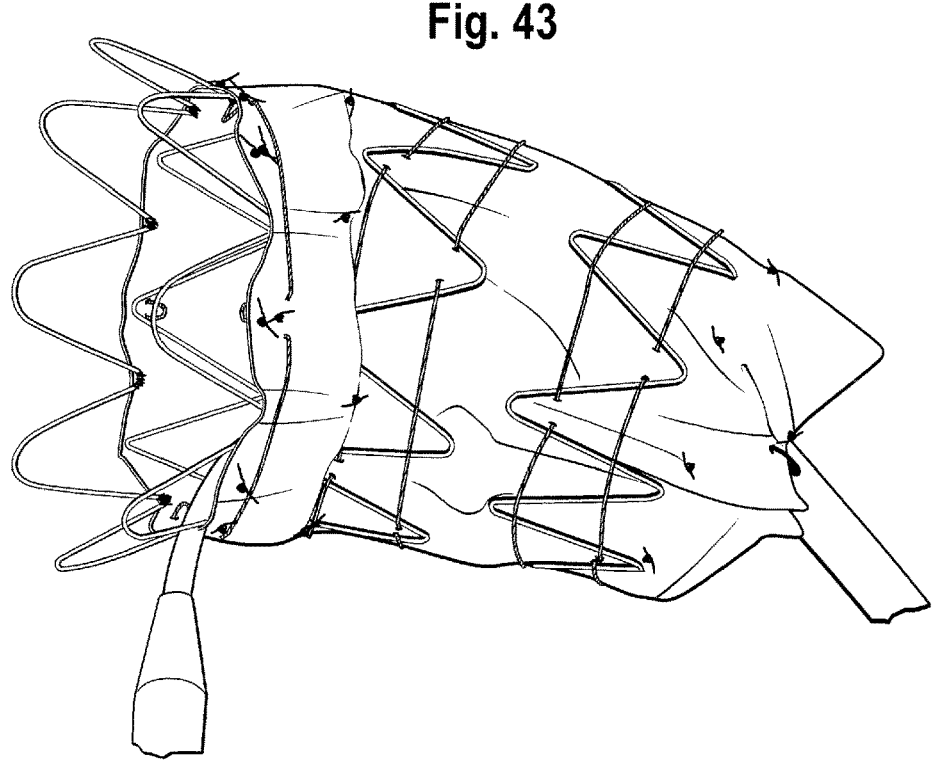

FIGS. 41 to 43 show side views of the stent graft as the constraining mechanism of the second intermediate stent 122 is released in a staggered circumferential and longitudinal fashion and the second intermediate stent expands.

As the release wires are withdrawn proximally of (in other words closer to the operator than) the points at which they are coupled to the distal apices of the distal end stent, the distal apices of the distal end stent are no longer constrained and can spring open. Because of the staggered nature of the withdrawal of the release wires, the apices of the distal end stent are released and spring open in stages, as the release wires release different sets of apices at different times. This is shown in FIGS. 45-48, and allows a gradual expansion process. In this embodiment, the scallop 80 is located in the vicinity of the first set of apices of the distal apices of the distal end stent to spring open, but this is not necessary in all embodiments.

Without wishing to be bound by theory, it is believed that the ordered release of the stents from their constraining mechanisms in this manner enables the expansion of each stent both to be guided by, and to assist, the expansion of the adjacent proximal stent, thereby enabling the stent graft to expand in a smooth and reliable manner into its desired position within the vessel.

As shown in FIGS. 25 and 26, once the release wires 42 have been withdrawn proximally of (in other words closer to the operator than) the constraining mechanism of the distal end stent, the entire stent graft can be fully deployed and the first covered stent is substantially aligned with the line 138.

As can be seen from the above, embodiments of the invention enable careful repositioning after retraction of the sheath but before full deployment and a smooth and accurate deployment of the stent graft. This is particularly advantageous in the ascending aorta where it is difficult to manipulate a deployment device owing to the significant curvature of the aortic arch, and where also it is important to ensure an accurate and reliable placement.

Despite the withdrawal of the release wires in a staggered fashion, the constriction elements in this embodiment still allow the stents to expand in a substantially symmetrical fashion. This has been found to cause a gradual transition from a constricted configuration to a released configuration, with a gradual increase in diameter. The release of all the constraining mechanisms is preferably performed as a quick procedure to minimize the risk of the blood flow dislodging the device as it is being deployed.

Although in the above description the release wires are withdrawn in a staggered fashion so each constraining mechanism is released in stages, it is possible for the release wires to be withdrawn together to cause all couplings of the stent graft to the release wires that are at substantially the same longitudinal positions to be released substantially together.

Although in the above embodiments each of the release wires operates all of the constraining mechanisms, in some embodiments there are different release wires for different constraining mechanisms. In such embodiments, each release wire may operate one or more constraining mechanisms, possibly in combination with one or more further release wires. One embodiment includes a set of release wires for operating the proximal-most and distal-most constraining mechanisms, and a separate set of release wires for operating the other constraining mechanisms.

In some embodiments, the proximal-most and distal-most constraining mechanisms may be released, in the manner described above, but after the other constraining mechanisms. In further embodiments, the proximal and distal end stents may each be retained by a retention mechanism and released in a different procedure from the constraining mechanisms which constrain the stents between them. For example, the proximal and distal end stents may be deployed after the constraining mechanisms which constrain the stents between them have been released. The retention mechanisms may be similar to the constraining mechanisms for the proximal and distal end stents described above and may include features of the constraining mechanisms discussed above. A retention mechanism actuation mechanism, which may be separate from but similar to, the actuation mechanism discussed above, may be provided including a plurality of retention mechanism release wires or rods, and each of the retention mechanisms may include a plurality of couplings to the retention mechanism release wires or rods, the retention mechanism release wires or rods being operable to be withdrawn from the couplings to release the retention mechanisms. In a similar manner to the release wires or rods discussed above, the retention mechanism release wires or rods may have ends which during withdrawal terminate at different longitudinal positions whereby to release different couplings of each of the retention mechanisms at different times whereby to release each of the retention mechanisms in stages. Preferably, the distal end stent is the last stent to be deployed.

Figure 44:
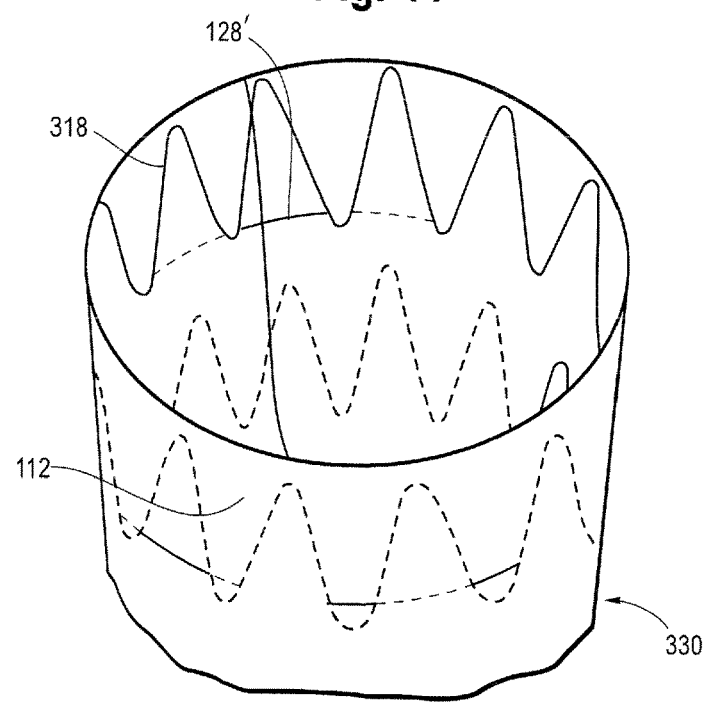
FIG. 44 is a schematic view of part of a stent graft in accordance with another embodiment of the invention.
Figure 45:
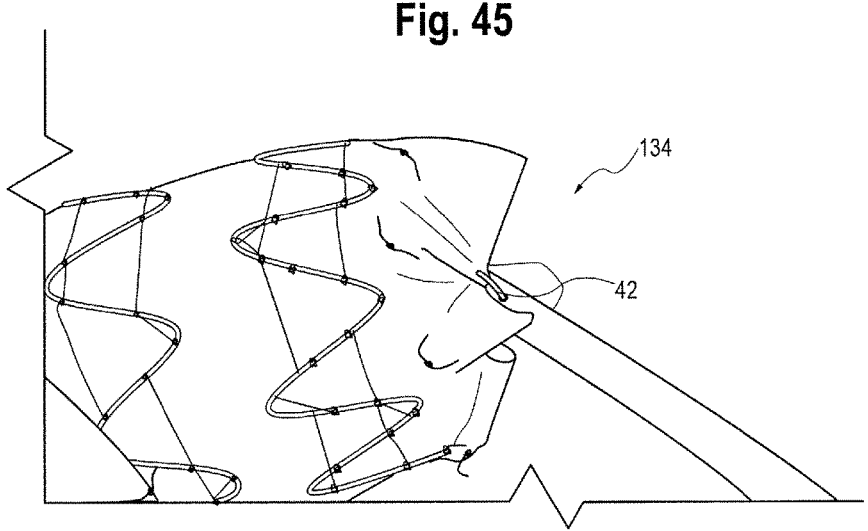
FIGS. 45 through 48 are perspective views of the sequential deployment of the distal end stent of the stent graft of FIG. 4 at various sequential stages of deployment.
Figure 46:
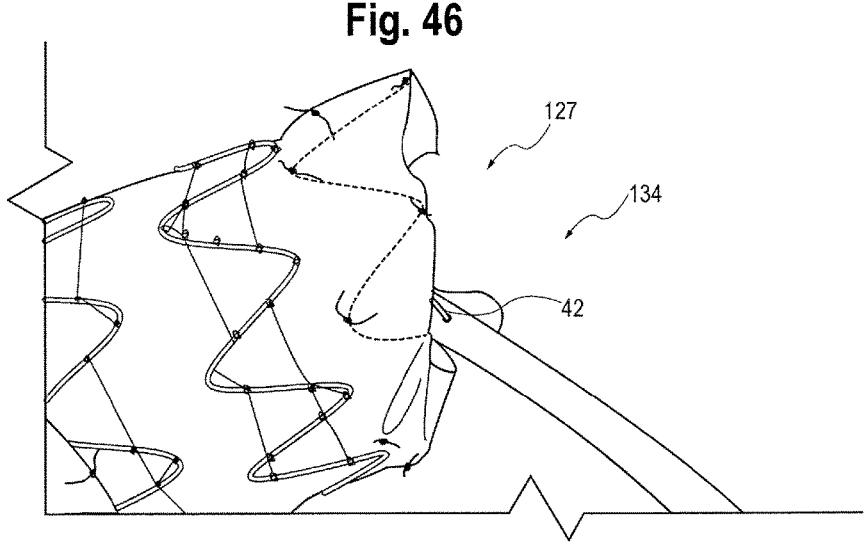
Figure 47:
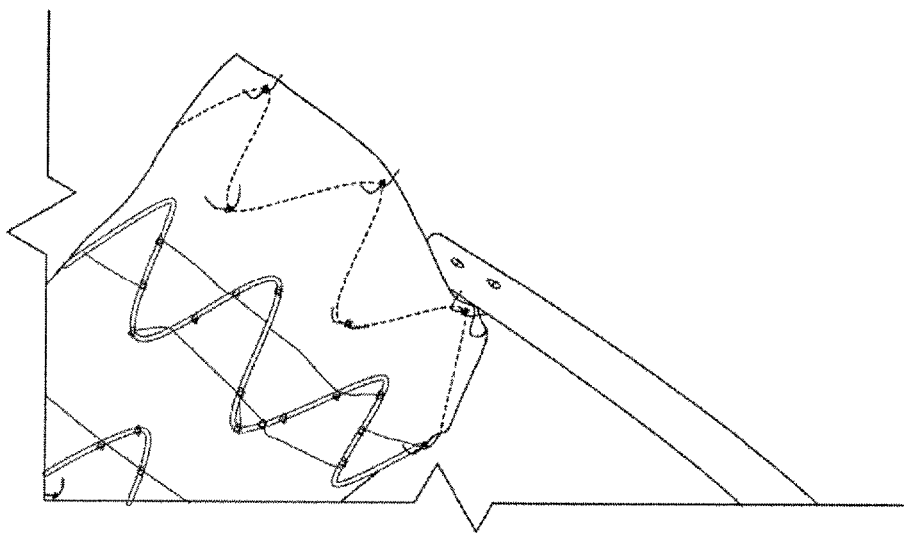
Figure 48:
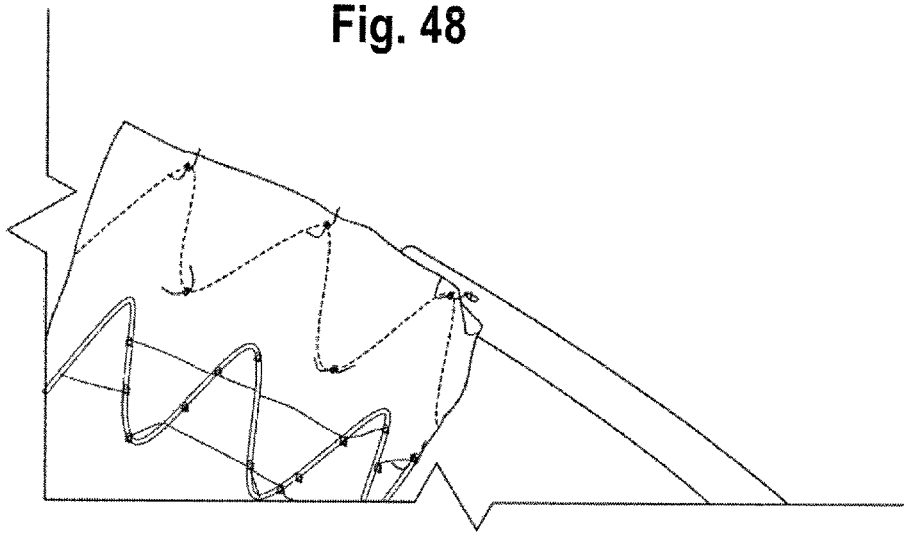

Furthermore, although each of the threads of the constriction elements is described as being a single thread that extends around substantially the entire circumference of the respective stent section, it is possible for one or more or all of these threads to be replaced by a plurality of threads each extending around a part of the circumference of the respective section of the respective stent and each being attached to a release wire 42 at a restraining location. One such embodiment is shown in FIG. 44, which shows a constriction element 330 for the first covered stent 318. In the embodiment of FIG. 44, although only three lengths are shown, there are provided for the constriction element 330 four lengths of suture thread 128' each attached to a plurality of stent apices. Each suture thread 128' is located generally on the outside of the graft material 112 apart from a length or bight which feeds to the inside of the graft material 112, although as described above it is not necessary for the threads to be outside the graft material in every embodiment. This length or bight can be fed through one of the openings 7 in the guide wire carrier 24 and restrained by a release wire therein. The other constriction elements for the stent graft may be correspondingly arranged. The threads do not always have to be attached to the apices of the stent, but can for example be attached to struts between the apices. However, the number of lengths of thread and the number of apices or struts to which each length of thread is attached can be varied.

It is not necessary in all embodiments for every constriction element to be directly attached to the stent that it is designed to constrict. For example, in some embodiments, one or more or all constriction elements can be configured to constrict the graft material, for example by attachment thereto, in proximity to the respective stent and thereby constrict the respective stent by virtue of the attachment of the stent to the graft material.

Furthermore, in some embodiments, one or more or all of the threads of the constriction elements can be replaced by a plurality of non-circumferential threads, each of the non-circumferential threads being at a restraining location and being tied to the respective release wire and attached to the graft and/or stent, thereby tying the medical device to the release wires at the restraining locations. In these embodiments, the constricting function is provided by the medical device being pulled radially inwards at the restraining locations and without a circumferential constriction element thread assisting in the constriction. However, a single thread extending around substantially the entire circumference is advantageous as it is believed to efficiently constrict the entire circumference of the stent graft.

Although the embodiments described above include first and second constriction elements for all intermediate stents, in some embodiments these stents, or at least some of these stents, are provided with a single constriction element which is preferably, but not necessarily, located at a longitudinally substantially central region of the respective stent. Nevertheless, these constriction elements are preferably configured to constrict substantially the full longitudinal extent of their respective stents.

In some embodiments, the constraining mechanism for the first covered stent 122' can be provided with first and second constriction elements as per the intermediate stents, or the constriction element of the first covered stent 122' can be located to constrict a distal section of the first covered stent in a manner corresponding to the second constriction element of the intermediate stents.

Furthermore, in some embodiments, one or more constriction elements corresponding to the constriction elements of the intermediate stents can be provided for the distal end stent 120 in addition to or instead of the constraining element for the distal end stent described above.

Although in the embodiments described above the proximal end stent is a bare stent, it is possible for the bare stent to be omitted, meaning that the first covered stent is also the proximal end stent. In such embodiments, the first covered stent can be constrained by a tri-fold constraining mechanism such as disclosed in U.S. Publication No. 2010/0114291, which is incorporated herein by reference in its entirety. This can be in addition to or instead of a constriction element such as described above. Preferably, in embodiments which do not have a bare stent at the proximal end of the stent graft, the first covered stent includes a constriction element at the distal section of the stent corresponding to the second constriction element 128 of the intermediate stents as described above as this has been found to provide a particularly reliable positioning for the proximal end stent, enabling the proximal end stent to expand against the walls of a vessel in which it is deployed so that the struts of the stent are substantially parallel to the vessel wall.

Although U.S. Publication No. discloses a tri-fold constraining mechanism primarily for the proximal stent, such a constraining mechanism can be used for the distal end stent of embodiments of the present invention instead of or in addition to the constraining mechanism described above.

In some embodiments, the stent graft can be provided with a mechanism for controlling the curvature of the stent graft such as disclosed in WO 2009/126227, which is incorporated herein by reference in its entirety.

In some embodiments, the proximal end of the graft can be provided in a sinusoidal or otherwise scalloped shape such as is disclosed in WO 2010/129685, which is incorporated herein by reference. This can assist in packing efficiency. It can also minimize loose material between the stent struts at the proximal end of the graft if the first covered stent is not quite at its full deployment diameter. This is often the case as it is generally preferred for a stent graft to be slightly oversized for the vessel so that it imparts a radially outward force on the vessel wall.

In some embodiments, it is possible to provide a scalloped edge at the proximal end of the graft, for example to provide for receiving a side branch prosthesis for example from the innominate artery. In such embodiments, it is possible to orient a curved delivery cannula with a spiral wire before withdrawing the sheath. After the sheath is withdrawn, it is possible to maneuver the stent graft as described above before full deployment in order to align the scallop for the side branch prosthesis with a wire guide to the innominate artery.

The term thread as used herein is intended to include any filamentary material which can perform the stated function and could, for example, be of conventional suture material, a multi-filamentary structure formed of yarns for example and of a natural or synthetic material such as cotton, other biocompatible material or a polymer material such as polyester, or a mono-filamentary structure of a natural material, other biocompatible material, a metal such as gold or an alloy such as Nitinol.

In some embodiments, the stent graft can include a prosthetic valve, for example a prosthetic heart valve can be positioned at a proximal end of the stent graft.

All optional and preferred features and modifications of the described embodiments and dependent claims are usable in all aspects of the invention taught herein. Furthermore, the individual features of the dependent claims, as well as all optional and preferred features and modifications of the described embodiments are combinable and interchangeable with one another.

The invention claimed is:

1. A stent graft deployment system comprising:
a delivery device having an operator end and a deployment end;
a stent graft disposed at the deployment end, the stent graft having a proximal end nearest the deployment end, a distal end toward the operator end, a generally tubular structure, a length, a proximal end stent at the proximal end of the stent graft, a distal end stent at the distal end of the stent graft, and at least one intermediate stent between the proximal end stent and the distal end stent;
a plurality of releasable constraining mechanisms arranged along the length of the stent graft, wherein a constraining mechanism of the plurality of constraining mechanisms extends circumferentially about a portion of the proximal end stent, the distal end stent, and the at least one intermediate stent to hold the proximal end stent, the distal end stent and the at least one intermediate stent in a constrained configuration; and
an actuation mechanism including a plurality of release wires or rods coupled to the constraining mechanisms to form a plurality of couplings between the release wires or rods and the constraining mechanisms about the circumference of the constraining mechanisms;
wherein the release wires or rods are configured to be withdrawn to release the couplings between the release wires or rods and the constraining mechanisms of the proximal stent in stages circumferentially, and thereafter to release the couplings between the release wires or rods and the constraining mechanism of the at least one intermediate stent in stages circumferentially, and thereafter to release the couplings between the release wires or rods and the constraining mechanism of the distal stent in stages circumferentially, such that the proximal stent, the at least one intermediate stent and the distal stent are each expanded in stages about their circumferences and longitudinally from the proximal end of the stent graft to the distal end of the stent graft.

2. The stent graft deployment system of claim 1, wherein each of the release wires or rods have ends that terminate at different longitudinal positions.

3. The stent graft deployment system of claim 1, wherein the proximal end stent and the distal end stent are provided with a single constraining mechanism and the at least one intermediate stent is provided with two constraining mechanisms.

4. The stent graft deployment system of claim 1, wherein each of the proximal end stent, the distal end stent, and the at least one intermediate stent have proximal and distal ends.

5. The stent graft deployment system of claim 4, wherein the proximal end stent and the distal end stent each have a single constraining mechanism.

6. The stent graft deployment system of claim 5, wherein the single constraining mechanism of the proximal end stent is circumferentially disposed about the proximal end of the proximal end stent and the single constraining mechanism of the distal end stent is circumferentially disposed about the distal end of the distal end stent.

7. The stent graft deployment system of claim 4, wherein the at least one intermediate stent has two constraining mechanisms.

8. The stent graft deployment system of claim 7, wherein the two constraining mechanisms comprise a first constraining mechanism disposed about the proximal end of the at least one intermediate stent and a second constraining mechanism disposed about the distal end of the at least one intermediate stent.

9. The stent graft deployment system of claim 1, wherein the release wires or rods are different lengths.

10. The stent graft deployment system of claim 1, wherein the release wires or rods are configured to be withdrawn at the same time.

11. A stent graft deployment system comprising:
a delivery device having an operator end and a deployment end;
a stent graft disposed at the deployment end, the stent graft having a proximal end nearest the deployment end, a distal end toward the operator end, a generally tubular structure, a length, a covered proximal end stent at the proximal end of the stent graft, a covered distal end stent at the distal end of the stent graft, and at least two intermediate stents between the covered proximal end stent and the covered distal end stent;
a plurality of releasable constraining mechanisms arranged along the length of the stent graft, wherein at least one of the plurality of constraining mechanisms extends circumferentially about a portion of each of the covered proximal end stent, the covered distal end stent, and each of the at least two intermediate stents to hold the covered proximal end stent, the covered distal end stent and the at least two intermediate stents in a constrained configuration; and
an actuation mechanism including a plurality of release wires or rods coupled to the constraining mechanisms to form a plurality of couplings between the release wires or rods and the constraining mechanisms about the circumference of the constraining mechanisms;
wherein the release wires or rods are configured to be withdrawn to release the couplings between the release wires or rods and the constraining mechanisms of the proximal stent in stages circumferentially, and thereafter to release the couplings between the release wires or rods and the constraining mechanism of the at least one intermediate stent in stages circumferentially, and thereafter to release the couplings between the release wires or rods and the constraining mechanism of the distal stent in stages circumferentially, such that the proximal stent, the at least one intermediate stent and the distal stent are each expanded in stages about their circumferences and longitudinally from the proximal end of the stent graft to the distal end of the stent graft.

12. The stent graft deployment system of claim 11, wherein each of the release wires or rods have ends that terminate at different longitudinal positions.

13. The stent graft deployment system of claim 11, wherein the proximal end stent and the distal end stent are provided with a single constraining mechanism and the at least two intermediate stents are each provided with two constraining mechanisms.

14. The stent graft deployment system of claim 11, wherein each of the proximal end stent, the distal end stent, and the at least two intermediate stents have proximal and distal ends.

15. The stent graft deployment system of claim 14, wherein the proximal end stent and the distal end stent each have a single constraining mechanism.

16. The stent graft deployment system of claim 15, wherein the single constraining mechanism of the proximal end stent is circumferentially disposed about the proximal end of the proximal end stent and the single constraining mechanism of the distal end stent is circumferentially disposed about the distal end of the distal end stent.

17. The stent graft deployment system of claim 14, wherein each of the at least two intermediate stents has two constraining mechanisms.

18. The stent graft deployment system of claim 17, wherein the two constraining mechanisms comprise a first constraining mechanism disposed about the proximal end of the at least one intermediate stent and a second constraining mechanism disposed about the distal end of the at least one intermediate stent.

19. The stent graft deployment system of claim 11, wherein the release wires or rods are different lengths and configured to be withdrawn at the same time.

20. A method for deploying a stent graft in stages, comprising:
  introducing a delivery device to a deployment region of a body vessel,
  the delivery device having an operator end, a deployment end, a stent graft disposed at the deployment end, the stent graft having a proximal end nearest the deployment end, a distal end toward the operator end, a generally tubular structure, a length, a proximal end stent at the proximal end of the stent graft, a distal end stent at the distal end of the stent graft, and at least one intermediate stent between the proximal end stent and the distal end stent, a plurality of releasable constraining mechanisms arranged along the length of the stent graft, wherein at least one of the plurality of constraining mechanisms extends circumferentially about a portion of each of the proximal end stent, the distal end stent, and the at least one intermediate stent to hold the proximal end stent, the distal end stent and the at least one intermediate stent in a constrained configuration, and an actuation mechanism including a plurality of release wires or rods coupled to the constraining mechanisms to form a plurality of couplings between the release wires or rods and the constraining mechanisms about the circumference of the proximal end stent, the distal end stent;
  withdrawing the release wires or rods in a direction from the deployment end to the operator end;
  releasing the couplings between the release wires or rods and the constraining mechanisms of the first stent in stages circumferentially, and thereafter releasing the couplings between the release wires or rods and the constraining mechanism of the at least one intermediate stent in stages circumferentially, and thereafter releasing the couplings between the release wires or rods and the constraining mechanism of the distal stent in stages circumferentially, such that the proximal stent, the at least one intermediate stent and the distal stent are each expanded in stages about their circumferences and longitudinally from the proximal end of the stent graft to the distal end of the stent graft.

* * * * *